United States Patent [19]

Ponsford et al.

[11] Patent Number: 4,647,558

[45] Date of Patent: Mar. 3, 1987

[54] ANTIBACTERIAL AGENTS, THEIR PREPARATION AND USE

[75] Inventors: Roger J. Ponsford; Michael J. Pearson, both of Horsham; Stephen C. Finch, Redhill, all of England

[73] Assignee: Beecham Group p.l.c., England

[21] Appl. No.: 459,675

[22] Filed: Jan. 20, 1983

[30] Foreign Application Priority Data

Jan. 22, 1982 [GB] United Kingdom ................. 8201752

[51] Int. Cl.[4] ................. C07D 205/08; C07D 401/12; C07D 403/04
[52] U.S. Cl. ................. 514/210; 540/355; 540/363
[58] Field of Search ................. 260/239 A, 245.4; 514/210; 540/355

[56] References Cited

U.S. PATENT DOCUMENTS

| 4,081,440 | 3/1978 | Kukolja | 260/239 A |
| 4,115,383 | 9/1978 | Cooper | 260/239 A |
| 4,133,808 | 1/1979 | Cooper | 260/239 A |

*Primary Examiner*—Mark L. Berch
*Attorney, Agent, or Firm*—Jacobs & Jacobs

[57] ABSTRACT

A monocyclic β-lactam antibiotic having a formamido substituent at the 3S-position, including compounds of the formula (I):

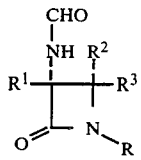

(I)

and salts thereof wherein R is —SO$_3$H; —PO(OH)Y wherein Y is C$_{1-6}$ alkoxy, hydroxy, aryloxy, C$_{1-6}$ alkyl or aryl;

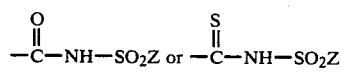

wherein Z represents C$_{1-6}$ alkyl or aryl;

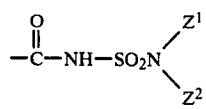

wherein Z$^1$ and Z$^2$ may be the same or different and each represents hydrogen, C$_{1-6}$ alkyl, aryl, amino or C$_{1-6}$ alkoxy, or Z$^1$ and Z$^2$ together form the residue of a heterocyclic ring; —OSO$_3$H; or

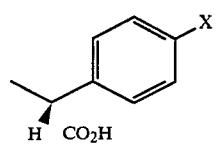

where X is hydrogen or hydroxy; R$^1$ is an amino, protected amino or carboxylic acylamino group, and R$^2$ and R$^3$ are independently selected from hydrogen or a hydrocarbon group of 1 to 18 carbon atoms.

12 Claims, No Drawings

ANTIBACTERIAL AGENTS, THEIR PREPARATION AND USE

This invention relates to β-lactam containing antibacterial agents and in particular to a class of monocyclic β-lactams having a 3S-formamido substituent. This invention further relates to processes for preparing such compounds and to compositions containing them. These compounds are of use in the treatment of bacterial infection in animals, for example mammals such as man.

The present invention provides a monocyclic β-lactam antibiotic having a formamido substituent at the 3S-position. Suitably the monocyclic β-lactam antibiotic is substituted at the 3R-position by an acylamino group.

Suitably the present invention provides the compounds of the formula (I):

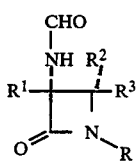
(I)

and salts thereof wherein R is —SO$_3$H; —PO(OH)Y wherein Y is C$_{1-6}$ alkoxy, hydroxy, aryloxy, C$_{1-6}$ alkyl or aryl;

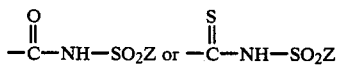

wherein Z represents C$_{1-6}$ alkyl or aryl,

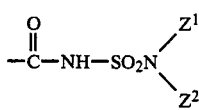

wherein Z$^1$ and Z$^2$ may be the same or different and each represents hydrogen, C$_{1-6}$ alkyl, aryl, amino or C$_{1-6}$ alkoxy, or Z$^1$ and Z$^2$ together form the residue of a heterocyclic ring; —OSO$_3$H; or

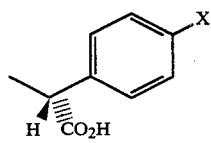

where X is hydrogen or hydroxy; R$^1$ is an amino, protected amino or carboxylic acylamino group, and R$^2$ and R$^3$ are independently selected from hydrogen or a hydrocarbon group of 1 to 18 carbon atoms.

Preferably R is —SO$_3$H.

Suitably R$^1$ is a carboxylic acylamino group such as found in antibacterially active penicillins or cephalosporins. Thus suitable groups R$^1$ include those of the sub-formulae (a), (b), (c), (d) and (e):

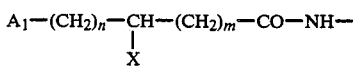
(a)

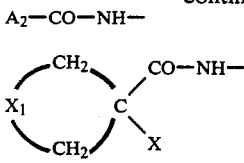
(b)
(c)

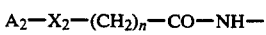
(d)

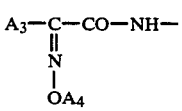
(e)

wherein n is zero, one or two, m is zero, one or two; A$_1$ is C$_{1-6}$ alkyl, C$_{3-6}$ cycloalkyl, C$_{4-7}$ cycloalkenyl, cyclohexadienyl, aryl or heteroaryl such as phenyl, substituted phenyl such as hydroxyphenyl, thienyl or pyridyl; X is a hydrogen, bromine or chlorine atom, or a carboxylic acid, carboxylate ester, sulphonic acid, tetrazolyl, azido, hydroxy, acyloxy, amino, acylamino, heterocyclylamino, ureido, guanidino or acylureido; A$_2$ is an aromatic group such as phenyl, 2,6-dimethoxyphenyl, 2-alkoxy-1-naphthyl, 3-arylisoxazolyl, isothiazolyl or 3-aryl-5-methylisoxazolyl group; X$_1$ is a CH$_2$OCH$_2$, CH$_2$SCH$_2$ or (CH$_2$)$_n$ group; X$_2$ is an oxygen or sulphur atom; A$_3$ is an aryl or heteroaryl group such as phenyl, substituted phenyl or aminothiazolyl; and A$_4$ is hydrogen, C$_{1-6}$ alkyl, C$_{3-6}$ cycloalkyl, arylaminocarbonyl, C$_{1-6}$ alkylaminocarbonyl, C$_{1-6}$ alkanoyl, C$_{1-6}$ alkoxycarbonyl, C$_{2-6}$ alkenyl, carboxy C$_{1-6}$ alkyl, C$_{1-6}$ alkylsulphonyl and di-C$_{1-6}$ alkylphosphatomethyl.

More suitably R$^1$ includes groups of the sub-formulae (f) and (g):

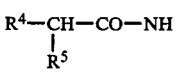
(f)

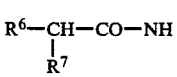
(g)

wherein R$^4$ is a phenyl, thienyl or phenoxy group; R$^5$ is a hydrogen atom or methyl group; R$^6$ is a phenyl, p-hydroxyphenyl, cyclohexadienyl, or a 5- or 6-membered heteroaryl or heterocyclyl group containing one to three heteroatoms selected from sulphur, oxygen or nitrogen, said group being optionally substituted by one, two or three substituents selected from hydroxy, amino, halo and C$_{1-6}$ alkoxy; and R$^7$ is a hydroxy, amino or carboxylic acid group or a phenyl, methylphenyl, indanyl or C$_{1-6}$ alkyl ester thereof, or is amino, ureido, acylamino or acylureido.

Examples of suitable groups R$^6$ include thienyl, pyridyl, phenyl, p-hydroxyphenyl and aminothiazolyl.

A particularly preferred group of the sub-formula (f) is the phenoxyacetamido group. Another particularly preferred group of the sub-formula (f) is the phenylacetamido group.

Suitably the ureido group in either the sub-formula (c) or sub-formula (g) is of the formula —NH—CO—NR8R9 wherein R8 is a hydrogen atom or a C$_{1-6}$ alkyl group and R9 is an organic group, or R8 and R$^9$ together with the nitrogen atom to which they are joined form an optionally substituted heteroaryl or heterocyclyl ring containing 1 or 2 nitrogen atoms.

Suitably $R^9$ is $C_{1-6}$ alkyl or an optionally substituted 5- or 6-membered heteroaryl or heterocyclyl group containing one or two nitrogen atoms.

Suitable substituents for $R^9$ and for the rings formed by $R^8$ and $R^9$ together include one, two or three groups selected from $C_{1-6}$ alkyl, $C_{2-6}$ alkenyl, $C_{2-6}$ alkynyl, $C_{3-6}$ cycloalkyl, optionally substituted phenyl, oxo, hydroxy optionally substituted such as $C_{1-6}$ alkoxy, $C_{2-6}$ alkenyloxy, $C_{3-6}$ cycloalkyloxy or phenoxy, mercapto optionally substituted such as phenylthio or $C_{1-6}$ alkylthio; or amino or substituted amino such as $C_{1-6}$ alkylamino, optionally substituted phenylamino, benzylamino or sulphonylamino for example $C_{1-6}$ alkyl sulphonylamino or p-aminosulphonylphenylamino. Alternatively two substituents on the ring $R^9$ or on the ring formed by $R^8$ and $R^9$ together may form the residue of a further carbocyclic or heterocyclic ring.

Suitably also X may be an acylamino or acylureido group, for example, of the sub-formula (h):

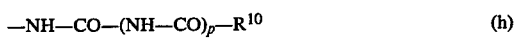

$$-NH-CO-(NH-CO)_p-R^{10} \qquad (h)$$

wherein p is zero or one and $R^{10}$ is a hydrogen atom or an organic group such as aryl, heteroaryl, heterocyclyl, $C_{2-6}$ alkenyl or $C_{1-6}$ alkyl.

Compounds of the formula (I) wherein $R^1$ is amino or protected amino have antibacterial activity but are envisaged mainly as useful intermediates in the preparation of compounds of the formula (I) wherein $R^1$ is carboxylic acylamino. "Protected amino" means that the amino moiety ($NH_2-$) is protected in conventional manner by a group or groups that may be removed under conventional conditions and would be suitable for use in the processes of this invention. Examples of suitable protected amino groups include hydrocarbyloxycarbonylamino such as t-butoxycarbonylamino and benzyloxycarbonylamino; and benzylideneamino such as $Ph-CH=N-$.

Suitably in the compounds of the formula (I) $R^2$ is a hydrogen atom. Suitably also $R^3$ is a hydrogen atom. Thus in a preferred aspect $R^2$ and $R^3$ are each hydrogen.

Alternatively $R^2$ and $R^3$ are independently selected from $C_{1-18}$ hydrocarbons, for example $C_{1-6}$ alkyl, $C_{2-6}$ alkenyl, $C_{2-6}$ alkynyl, $C_{3-8}$ cycloalkyl, aryl, aryl($C_{1-6}$)alkyl, aryl($C_{2-6}$)alkenyl, heterocyclyl and heterocyclyl ($C_{1-6}$)alkyl, any of such groups being optionally substituted. Suitably the above named heteroaryl and heterocyclyl rings contain not more than 10 ring atoms, up to 4 of which are selected from oxygen, sulphur and nitrogen.

One particularly preferred sub-group of compounds is that of the formula (II):

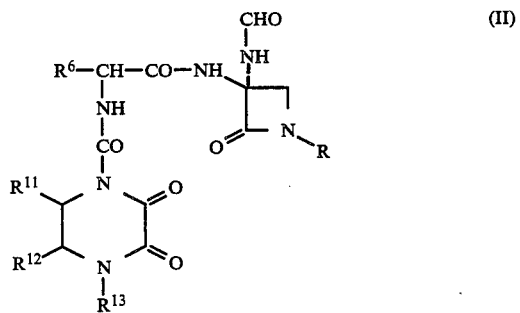

and salts thereof wherein R and $R^6$ are as hereinbefore defined, $R^{11}$ and $R^{12}$ are independently selected from hydrogen, $C_{1-6}$ alkyl, halo, amino, hydroxy or $C_{1-6}$ alkoxy, and $R^{13}$ is hydrogen, $C_{1-6}$ alkyl, or aralkyl such as benzyl. Suitably $C_{1-6}$ alkyl groups for the groups $R^{11}$, $R^{12}$ and $R^{13}$ include methyl, ethyl, n- and iso-propyl, and n, sec-, iso- and tert-butyl. Preferably $R^{13}$ is ethyl. Preferably $R^{11}$ and $R^{12}$ are each hydrogen. Preferably R is $-SO_3H$.

A further preferred sub-group of compounds is that of the formula (III):

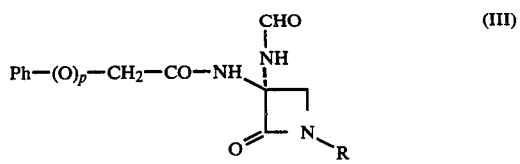

and salts thereof wherein R is as hereinbefore defined and p is zero or one.

Preferably R is $-SO_3H$ or a salt thereof.

Another preferred sub-group of compounds is that of the formula (IV):

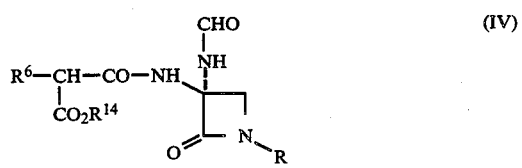

and salts thereof wherein $R^{14}$ is a cation, hydrogen atom or a benzyl, phenyl, methylphenyl or indanyl group, and R and $R^6$ are as hereinbefore defined.

Preferably R is $-SO_3H$.

Yet another preferred sub-group of compounds is that of the formula (V):

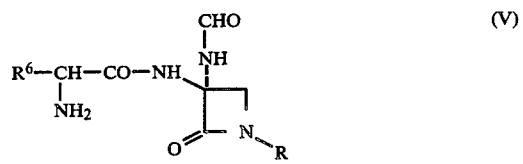

and salts thereof wherein R and $R^6$ are as defined hereinabove.

Preferably R is $-SO_3H$.

Another class of preferred compounds is that of the formula (VI):

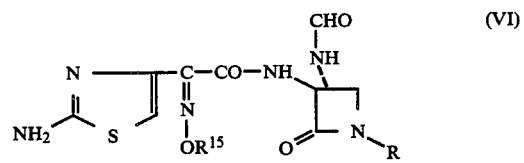

and salts thereof wherein R is as hereinbefore defined and $R^{15}$ is hydrogen, $C_{1-6}$ alkyl such as methyl and ethyl, $C_{1-6}$ alkanoyl such as formyl and acetyl, methoxycarbonyl, ethenyl, methanesulphonyl, carboxy($C_{1-6}$)alkyl such as carboxymethyl, carboxyethyl and 2-carboxyprop-2-yl, or dimethylphosphatomethyl.

Preferably R is $-SO_3H$.

The major utility of the compounds of the formulae (I)–(VI) and salts thereof is as pharmaceuticals and accordingly the salts are preferably pharmaceutically acceptable. The compounds of this invention both pharmaceutically acceptable and non-pharmaceutically acceptable may be used as intermediates, for example for the preparation of pharmaceutically acceptable salts of this invention, or in non-pharmaceutical usage such as a disinfectant or paint additive.

Suitable pharmaceutically acceptable salts include metal salts such as alkali metal salts for example sodium and potassium, alkaline earth metal salts such as calcium and magnesium, and ammonium and substituted ammonium salts, for example tetrabutylammonium and pyridinium.

In another aspect of this invention there is provided a pharmaceutical composition which comprises a compound of the formula (I) or a pharmaceutically acceptable salt thereof and a pharmaceutically acceptable carrier.

The composition may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for administration may be in unit dose presentation form, and may contain conventional excipients such as binding agents, for example syrup, acacia, gelatin, sorbitol, tragacanth, or polyvinylpyrrolidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parental suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration.

The compound of formula (I) in pharmaceutically acceptable form may be the sole therapeutic agent in the compositions of the invention or a combination with other antibiotics or with a $\beta$-lactamase inhibitor may be employed.

Suitable $\beta$-lactamase inhibitors include the compounds of the formula (VII) and pharmaceutically acceptable salts and esters thereof:

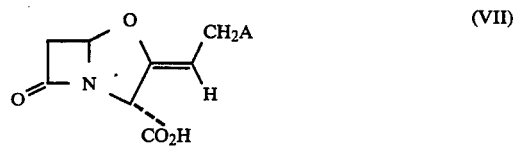

(VII)

wherein A is hydroxy, substituted hydroxy, mercapto, substituted mercapto, amino, mono- or di-hydrocarbyl-substituted amino, or mono- or di-acylamino.

Further suitable $\beta$-lactamase inhibitors include penicillanic acid 1,1-dioxide and salts and in-vivo hydrolysable esters thereof, $6\beta$-bromopenicillanic acid and salts and in-vivo hydrolysable esters and $6\beta$-iodopenicillanic acid and salts and in-vivo hydrolysable esters thereof.

Such compositions of this invention comprising a $\beta$-lactamase inhibitor are formulated in conventional manner.

The present invention further provides a process for the preparation of a compound of the present invention which process comprises formulating a monocyclic $\beta$-lactam having an amino substituted at the 3-position.

In another aspect the present invention provides a process for the preparation of a compound of the formula (I) wherein R is a sulphonic acid group or salt thereof which process comprises the sulphonation of a compound of the formula (VIII):

(VIII)

or reactive derivative thereof, wherein $R^1$, $R^2$ and $R^3$ are as hereinbefore defined, and thereafter if necessary:

(i) converting a compound of the formula (I) wherein $R^1$ is amino or protected amino to a compound of the formula (I) wherein $R^1$ is carboxylic acylamino, (ii) forming a pharmaceutically acceptable salt.

The sulphonation reaction may be conveniently performed using a sulphur trioxide complex, examples of which include pyridine-sulphur trioxide, dimethylformamide-sulphur trioxide, trimethylamine-sulphur trioxide, lutidine-sulphur trioxide, dioxan-sulphur trioxide and chlorosulphonic acid-sulphur trioxide. A preferred reagent is pyridine-sulphur trioxide.

The sulphonation reaction is performed at a non-extreme temperature such as 0°–80° C., more suitably 10°–50° C. and conveniently at ambient temperature. Normally the reaction is performed in a solvent, for example an organic solvent such as dimethylformamide, dichloromethane, chloroform, dioxan, tetrahydrofuran, or mixtures thereof. Of these the preferred solvent is dioxan. reaction may lead to the preparation of a specific salt of the β-lactam, for example where the reagent used is pyridine-sulphur trioxide, the salt formed is the pyridinium salt. This may be converted to any other desired salt using conventional methods of ion-replacement, for example using ion-exchange resin, ion-pair extraction, crystallisation and precipitation.

Compounds of the formula (I) wherein $R^1$ is protected amino may be converted to compounds of the formula (I) wherein $R^1$ is carboxylic acylamino via the intermediacy of the compounds of the formula (I) wherein $R^1$ is amino.

Suitable amino-protecting groups include those known in the β-lactam art to be convertible to amino, for example hydrogenolysable groups, such as benzyloxycarbonylamino.

Compounds of the formula (I) wherein $R^1$ is carboxylic acylamino may be prepared by the reaction of a compound of the formula (I) wherein $R^1$ is amino or a derivative thereof that permits N-acylation to take place, with an N-acylating derivative of a carboxylic acid of the formula (IX):

$$R^{16}CO_2H \qquad (IX)$$

wherein $R^{16}$ is an organic group and any reactive group is optionally protected, and thereafter if necessary, removing any protecting group.

Suitable groups which permit acylation to take place and which are optionally present on the amino group $R^1$ includes N-silyl, N-stannyl and N-phosphorus groups, for example trialkylsilyl groups such as trimethylsilyl, trialkyltin groups such as tri-n-butyl-tin, groups of the formula $-PR^aR^b$ wherein $R^a$ is an alkyl, alkoxy, haloalkyl, aryl, aralkyl, haloalkoxy, aryloxy, aralkyloxy or dialkylamino group, $R^b$ is the same as $R^a$ or is halogen or $R^a$ and $R^b$ together form a ring: suitable such phosphorus groups being $-P(OC_2H_5)_2$, $-P(C_2H_5)_2$,

A reactive N-acylating derivative of the acid (IX) is employed in the above process. Suitable N-acylating derivatives include an acid halide, preferably the acid chloride or bromide. Acylation with an acid halide may be effected in the presence of an acid binding agent for example molecular sieve or a pyridine or a tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as aqueous acetone, ethyl acetate, dimethylacetamide, dimethylformamide, acetonitrile, dichloromethane, 1,2-dichloroethane, or mixtures thereof.

Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (IX) or a salt thereof with a halogenating (eg. chlorinating or brominating) agent such as phosphorus pentachloride, thionyl chloride or oxalyl chloride.

Alternatively, the N-acylating derivative of the acid (IX) may be a symmetrical or mixed anhydride. Suitable mixed anhydrides are alkoxyformic anhydrides, or anhydrides with, for example carbonic acid mono-esters, trimethyl acetic acid, thioacetic acid, diphenylacetic acid, benzoic acid, phosphorus acids such as phosphoric or phosphorous acids, sulphuric acid or aliphatic or aromatic sulphonic acids such as p-toluenesulphonic acid. The mixed or symmetrical anhydrides may be generated using N-ethoxycarbonyl-2-ethoxyl-2-ethoxy-1,2-dihydroquinoline. When a symmetrical anhydride is employed, the reaction may be carried out in the presence of 2,6-lutidine as catalyst.

Alternatively N-acylating derivatives of acid (IX) are the acid azide, or activated esters such as esters with 2-mercaptopyridine, 2-mercaptothiazoline, cyanomethanol, p-nitrophenol, 2,4-dinitrophenol, thioalcohols such as thiophenol, methanethiol, ethanethiol and propanethiol, halophenols, including pentachlorophenol, monomethoxy- or phenol or 8-hydroxyquinoline, N-hydroxysuccinimide or 1-hydroxybenztriazole; or amides such as N-acylsaccharins or N-acylphthalimides; or an alkylidine iminoester prepared by reaction of the acid (IX) with an oxime.

Other reactive N-acylating derivatives of the acid (IX) include the reactive intermediate formed by reaction in situ with a condensing agent such as a carbodiimide, for example N,N-dimethyl-, dipropyl- or diisopropylcarbodiimide, N,N'-di-cyclohexylcarbodiimide, or N-ethyl-N'-α-dimethylaminopropylcarbodiimide; a suitable carbonyl compound, for example N,N'-carbonyldiimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonylethoxy-1,2-dihydroquinoline. Other condensing agents include Lewis acids (for example $BBr_3$-$C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

In a further aspect the present invention provides a process for the preparation of a compound of the formula (I) which process comprises the formylation of a compound of the formula (X):

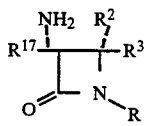
 (X)

or salt thereof or derivative thereof that permits N-formylation to take place, wherein R, $R^2$ and $R^3$ are as hereinbefore defined and any reactive groups may be protected, and $R^{17}$ is a carboxylic acylamino group or a protected amino group and thereafter if desired:

(i) converting a compound of the formula (I) wherein $R^1$ is not amino into a compound of the formula (I) wherein $R^1$ is amino;

(ii) removing any protecting group on R;

(iii) forming a pharmaceutically acceptable salt.

Suitable formylating agents include mixed anhydrides such as formic acetic anhydride. The reaction may be suitably performed at a depressed temperature such as $-50°$ to $+10°$ C. in an aprotic solvent, for example dichloromethane, tetrahydrofuran, chloroform, dimethylformamide, hexamethylphosphoramide or dimethylsulphoxide. Suitably a tertiary base is present such as a base of the pyridine type, for example pyridine, lutidine or picoline.

Compounds of the formula (VIII) may be prepared by the formylation of a compound of the formula (XI):

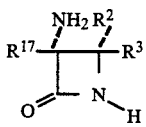
 (XI)

or derivative thereof that permits N-formylation to take place, wherein $R^2$, $R^3$ and $R^{17}$ are as hereinbefore defined; and thereafter if desired, converting a compound of the formula (VIII) wherein $R^1$ is not amino to a compound of the formula (VIII) wherein $R^1$ is amino.

Suitable methods of formylation are as described hereinabove with respect to the compound of the formula (X).

It is preferred that the β-lactam nitrogen is in the form of —NH— or a silyl derivative thereof.

Compounds of the formulae (X) and (XI) may be prepared by the reaction of a corresponding compound of the formula (XII):

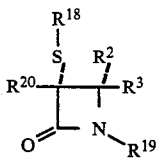
 (XII)

wherein $R^{20}$ is carboxylic acylamino or protected amino such as benzyloxycarbonylamino or t-butoxycarbonylamino, $R^2$ and $R^3$ are as hereinbefore defined, $R^{19}$ is hydrogen, a protecting group or a group R or a salt thereof, and $R^{18}$ is $C_{1-6}$ alkyl, aryl or benzyl; with anhydrous ammonia in the presence of a metal ion such as mercury, silver, thallium, lead or copper.

Suitably $R^{18}$ is $C_{1-6}$ alkyl such as a methyl, ethyl, n- or iso-propyl, or n-, sec-, iso- or tert-butyl group. A preferred alkyl group is methyl.

Suitably $R^{18}$ is an aryl group such as phenyl optionally substituted by $C_{1-6}$ alkyl, $C_{1-6}$ alkoxy, halo or nitro. Preferably $R^{18}$ is phenyl, o-, m- or p-methylphenyl, or o-, m- or p-nitrophenyl. A particularly preferred group $R^{18}$ is p-methylphenyl.

Suitable solvents in which the reaction may be performed are aprotic for example diethyl ether, tetrahydrofuran, dimethylformamido and hexamethylphosphoramide. Normally the reaction is performed under an inert atmosphere and at an ambient or depressed temperature such as $-100°$ C. to $+30°$ C. the course of the reaction may be followed by conventional methods such as thin layer chromatography and terminated when an optimum quantity of desired product is present in the reaction mixture.

The preferred metal ion for use in this reaction is the mercuric ion, aptly in the form of mercuric acetate.

Alternatively compounds of the formulae (X) and (XI) may be prepared by the reaction of a corresponding compound of the formula (XIII):

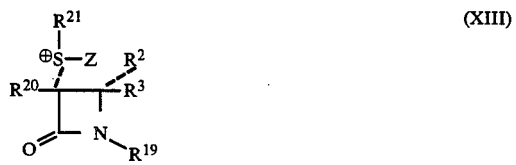
 (XIII)

wherein $R^{20}$, $R^2$, $R^3$ and $R^{19}$ are as hereinbefore defined, Z is chloro or bromo and $R^{21}$ is $C_{1-3}$ alkyl or benzyl; with a source of ammonia. The compounds of the formula (XIII) may be prepared by the reaction of a compound of the formula (XIV):

 (XIV)

wherein $R^{20}$, $R^2$, $R^3$, $R_{19}$ and $R^{21}$ are as hereinbefore defined, with a halogenating agent such as chlorine in an inert solvent, for example dichloromethane, at a depressed temperature such as $-80°$ C. to $-30°$ C.

A preferred method of preparation of the compounds of the formulae (X) and (XI) comprises the reaction of a compound of the formula (XV):

 (XV)

wherein $R^2$, $R^3$, $R^{20}$ and $R^{19}$ are as hereinbefore defined, and $R^{22}$ is a $C_{1-6}$ alkyl, aryl or benzyl group; with anhydrous ammonia or an amine of the formula (XVI):

$R^{23}$—$NH_2$   (XVI)

wherein $R^{23}$ is a removable protecting group such as benzyl; and thereafter if necessary removing any protecting group to form either the compound of the formula (X) or (XI).

Suitably such a reaction is performed at a non-extreme temperature for example 0° C.–60° C., normally 10° C.–40° C. and preferably ambient. The reaction is conveniently performed in an aprotic solvent such as tetrahydrofuran or dioxan.

The compounds of the formula (XV) may be prepared by the oxidation of a compound of the formula (XII) as hereinbefore defined. Such oxidation may be conveniently performed in conventional manner, for example using a per-acid such as peracetic acid or m-chloroperbenzoic acid, suitably at an ambient or depressed temperature. Suitable solvents for such a sulphoxidation include ethyl acetate, chloroform, dichloromethane, dioxan and tetrahydrofuran.

Examples of suitable protecting groups for the group $R^{19}$ include those known in the art as being cleavable to provide the —NH—. Mention may be made of silyl groups such as trimethylsilyl, tertiarybutyldimethylsilyl, and tri-isopropylsilyl. A preferred protecting group is (p-methoxymethoxy)phenyl which is removable by cerium ammonium nitrate. Other protecting groups of interest include those cleavable by methanolysis such as —C(CO$_2$R)=O (This moiety may be derived from groups of the type —C(CO$_2$R)=(CH$_3$)$_2$). Further suitable protecting groups include C$_{1-6}$ alkoxy and benzyloxy. A further suitable protecting group is 2,4-dimethoxybenzyl which is removable with potassium persulphate.

Compounds of the formula (XII) may be prepared by methods analogous to those known for the preparation of 7-α-thiocephalosporins and 6-α-thiopenicillins, from the compounds of the formula (XVII):

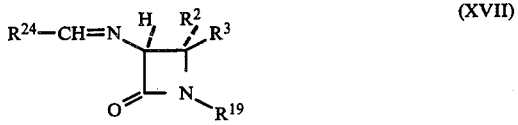
(XVII)

wherein $R^2$, $R^3$ and $R^{19}$ are as hereinbefore defined and $R^{24}$ is an optionally substituted aromatic ring. In such a reaction preferably $R_{19}$ is (p-methoxymethoxy)phenyl or a group such as —C(CO$_2$R)=O. If $R^{19}$ is silyl then it is preferred to use a strong non-nucleophilic base such as diazabicyclononene or diazabicycloundecene in a halogenated hydrocarbon for example dichloromethane, and suitably use a reagent such as CH$_3$S—SO$_2$—CH$_3$.

Suitably $R^{24}$ is p-nitrophenyl.

Compounds of the formula (XVII) may be prepared by reaction of a compound of the formula (XIX):

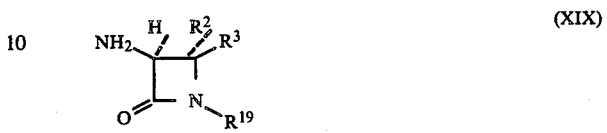
(XIX)

wherein $R^2$, $R^3$ and $R^{19}$ are as hereinbefore defined, with a compound of the formula (XX):

$$R^{24}\text{—CHO} \qquad (XX)$$

wherein $R^{24}$ is as hereinbefore defined.

Such reaction is conveniently performed in an inert solvent such as benzene toluene, dimethylformamide or acetonitrile, and may be conducted at ambient or an elevated temperature, for example 15° C. to 110° C. This reaction is an equilibrium reaction involving the formation of water, so the reaction is aided by removing the water during the course of the reaction, for example by azeotropic distillation or by the presence of a drying agent.

It should be realised that the group $R^1$ may be converted to another group $R^1$ at any convenient stage of the overall process of this invention by for example the general methods of deprotection and/or acylation outlined previously in this specification. Similarly the —SO$_3$H moiety may be introduced at any convenient stage of the overall process by the general methods of sulphonation referred to previously.

The compounds of the formula (XIX) may be prepared for example by the methods disclosed and discussed in UK Patent Application Publication No. 2071650A or the methods exemplified hereinafter which methods are summarised by the following Schemes.

SCHEME 1

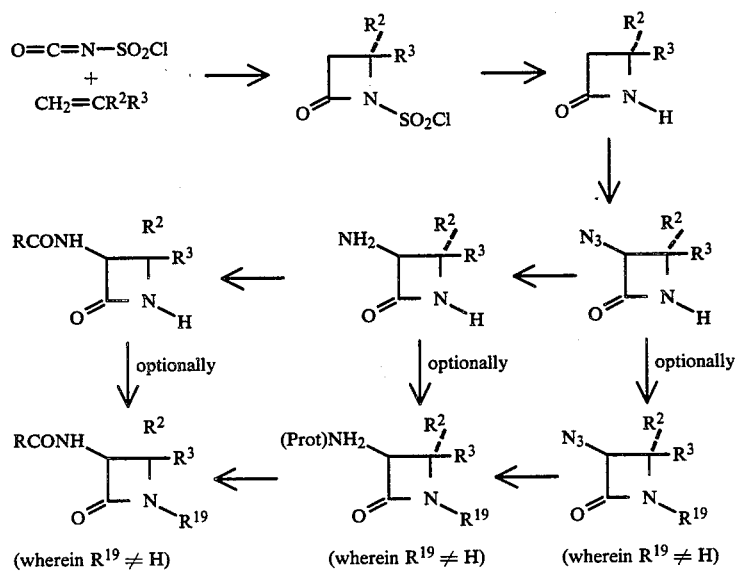

SCHEME 1

(Prot = optionally protected)

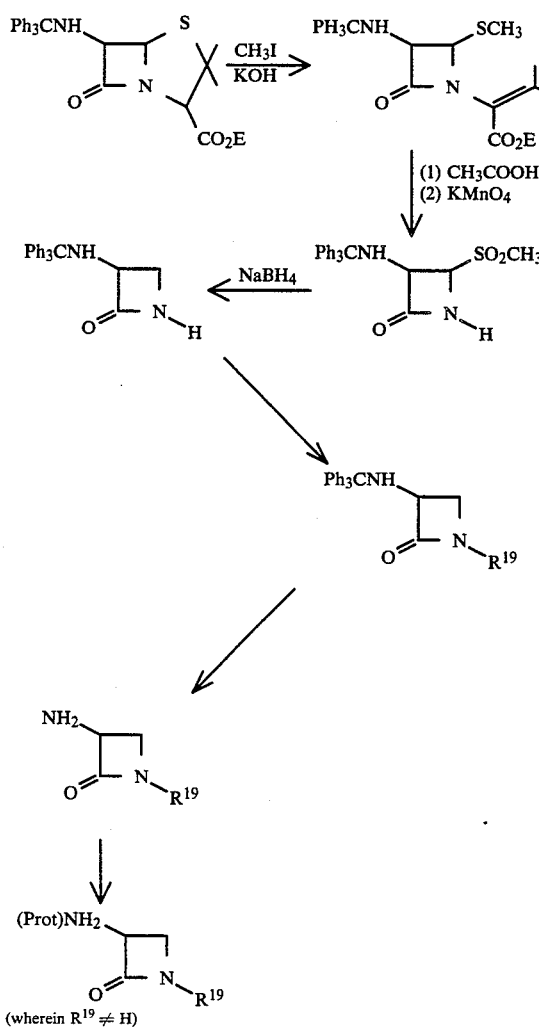

SCHEME 3
Applicable when at least one of R² and R³ is hydrogen.

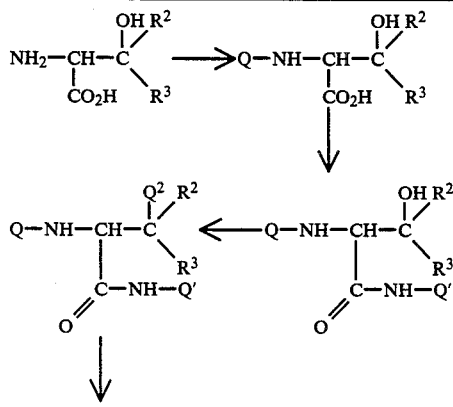

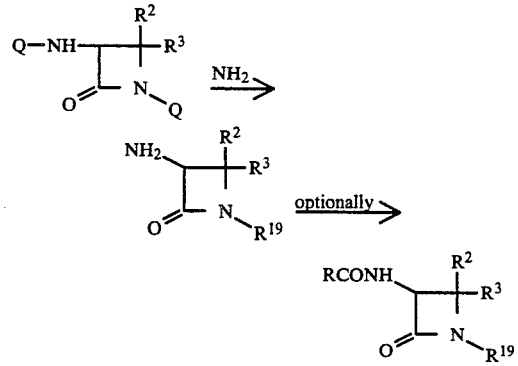

Q and Q' are protecting groups
Q² is a leaving group

A preferred variant of Scheme 3 is that where the nitrogen atom is protected as a phthalimido group (that is, Q—NH— is replaced by phthalimido). This prevents by-products arising from the intramolecular cyclization of the side-chain —NH— moiety.

For convenience we have only depicted one enatiomer of the monocyclic β-lactams described herein (with the exception of compounds (17)–(20) in the examples hereinafter). These enantiomers are believed to be the more active enantiomers. Resolution may be performed using conventional methods at any appropriate stage of the synthetic sequence.

EXAMPLE 1

(DL)-2-Benzyloxycarbonylamino-3-hydroxy-N-p-methoxymethoxyphenyl propionamide (1)

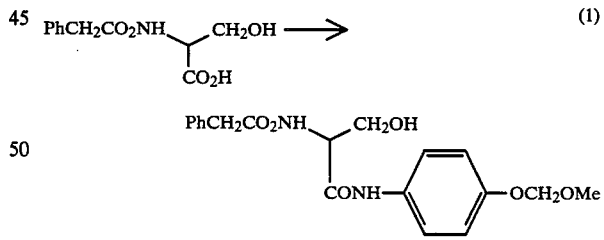

(DL)-Benzyloxycarbonylserine (42.67 g) was dissolved in dry tetrahydrofuran (300 ml) and p-methoxymethoxyaniline (27.54 g) added. The mixture was cooled to 0° C. and treated with dicyclohexylcarbodiimide (40.79 g) in dichloromethane (100 ml). The solution was warmed to room temperature and after 30 min the solid was removed and the filtrate evaporated. Trituration of the residue with ether gave a white solid (1) (59.17 g) slightly contaminated with dicyclohexylurea, but sufficiently pure for the next stage of the process; $\nu_{max}$ (Nujol) 3425, 3280, 1700, 1675 and 1660 cm$^{-1}$; $\delta$(CDCl$_3$) 3.38 (3H, s), 3.75 br (1H, s, becomes d, J 5.5 Hz on D$_2$O exch.), 4.34 (1H, m, becomes t, J 5.5 Hz on D$_2$O exch.), 4.76 br (1H, s, exch. D$_2$O), 5.07 (2H, s), 6.76

(1H, d, J 9 Hz, exch. D₂O), 6.9 (2H, d, J 8 Hz), 7.3 (5H, s), 7.49 (1H, d, J 8 Hz) and 9.48 (1H, s, exch. D₂O).

EXAMPLE 2

[3RS]-3-Benzyloxycarbonylamino-1-(p-methoxymethoxyphenyl)-azetidin-2-one (2)

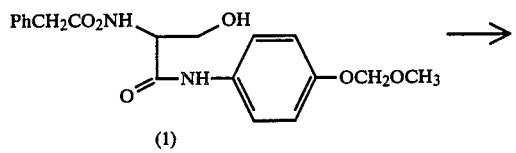

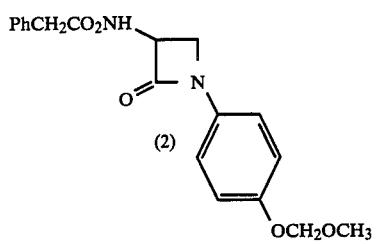

The amide (1) (4.94 g) was dissolved in dry tetrahydrofuran (150 ml) and the solution cooled to 0° C. Triphenylphosphine (3.8 g) was added, followed by the dropwise addition of diethyl azodicarboxylate (2.53 g) in tetrahydrofuran (5 ml). The solution was warmed to room temperature and after 15 min poured into ethyl acetate-water. The organic layer was separated, washed with brine, dried and evaporated. Chromatography on silica using ethyl acetate/methylene dichloride mixtures gave material which on recrystallisation from ethyl acetate-hexane provided in β lactam (2) (1.75 g), mp 153°–154° C.;

$\nu_{max}$ (CHCl₃) 3430, 1750 and 1730 cm⁻¹;

δ(CDCl₃) 3.44 (2H, s), 3.55 (1H, dd, J 5.5 and 3 Hz), 3.88 (1H, dd), 4.91 (1H, m), 5.55 (1H, m) and 6.9–7.5 (10H, m).

EXAMPLE 3

(3RS)-3-Amino-1-(p-methoxymethoxyphenyl)azetidin-2-one (3)

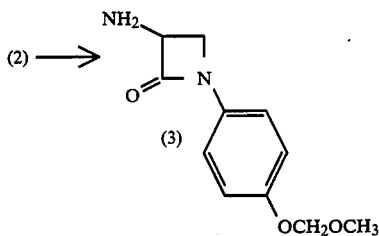

The lactam (2) (3.2 g) was dissolved in dry dioxan (100 ml) and hydrogenated over 10% palladium/charcoal (1.0 g) until the uptake of hydrogen ceased. The mixture was filtered through Kieselguhr and the filtrate was evaporated to give a white solid (3) (1.95 g);

$\nu_{max}$ (CHCl₃) 3365, 1738 cm⁻¹;

δ(CDCl₃) 1.74 (2H, s, exch. D₂O), 3.31 (1H, d, J 6.5 and 3 Hz), 3.44 (2H, s), 3.88 (1H, dd, J 6.5 and 6 Hz), 4.3 (1H, dd, J 6 and 3 Hz), 5.11 (2H, s), 6.98 (2H, d, J 9 Hz) and 7.17 (2H, d, J 9 Hz).

EXAMPLE 4

(3RS)-1-(p-Methoxymethoxyphenyl)-3-phthalimidoacetidin-2-one (6)

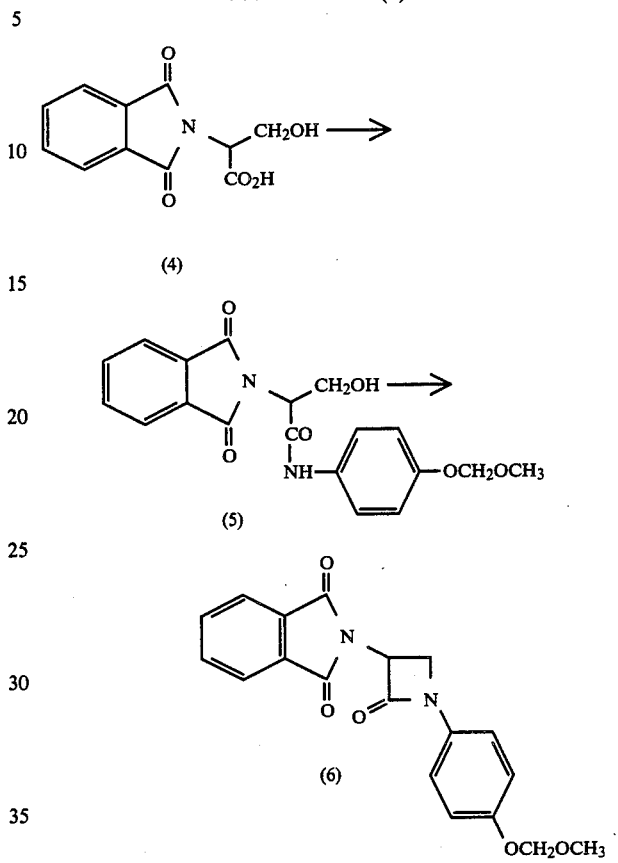

N-Phthaloylserine (4)(13.38 g; ca 80% pure by nmr) and p-methoxymethoxyaniline (6.96 g) were dissolved in dichloromethane (120 ml) and tetrahydrofuran (10 ml). The solution was then cooled to 0° C. and treated with dicyclohexylcarbodi-imide in dichloromethane (20 ml). The reaction mixture was allowed to warm to room temperature and after 1.5 h the solid was removed and the filtrate evaporated. The crude product (5) was sufficiently pure for the next step, and was dissolved in dry tetrahydrofuran (300 ml) at 0° C. Triphenyl-phosphine (17.88 g) was added followed by the dropwise addition of diethyl azodicarboxylate (11.65 g) in tetrahydrofuran (30 ml). The reaction mixture was allowed to warm to room temperature and after 0.5 h the solvent was evaporated off and the residue chromatographed on silica to provide (6) as a crystalline solid (B 12 g), m.p. 156° C.; $\nu_{max}$ (Nujol), 1790 (weak), 1740, 1720 cm⁻¹; δ(CDCl₃) 3.45 (3H, s), 4.0 (2H, d, J 5 Hz), 5.13 (2H, s), 5.46 (1H, t, J 5 Hz), 7.01 (2H, d, J 9 Hz), 7.35 (2H, d, J 9 Hz), and 7.65–7.95 (4H, m). (Found: C, 64.7; H, 4.5; N, 7.9. C₁₉H₁₆N₂O₅ requires C, 64.8; H, 4.5; N, 8.0%).

EXAMPLE 5

(3RS)-3-Amino-1-(p-methoxymethoxyphenyl)azetidin-2-one (3)

The lactam (6) (7.04 g) was dissolved in chloroform (80 ml) and N-methylhydrazine (2.02 g) added. The solution was stored at room temperature in the dark for 66 hours. The precipitated solid was filtered off. The filtrate was evaporated and the residue triturated with ether to provide (3) (4.04 g), identical to that described in Example 3.

EXAMPLE 6

(3RS)-1-pMethoxymethoxyphenyl-3-N-p-nitrobenzylideneamino-azetidin-2-one (7)

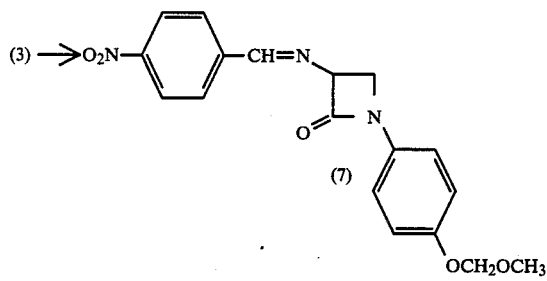

A solution of the amine (3) (2.64 g) and p-nitrobenzaldehyde (1.80 g) in an anhydrous mixture of toluene (100 ml) and dichloromethane (20 ml) was stirred for 20 hours at room temperature over 4A molecular sieves. The reaction mixture was then filtered and the filtrate evaporated to dryness. The residue was recrystallised from ethyl acetate-hexane to afford the product (7) as pale yellow needles (3.7 g). m.p. 139°–140° $\nu_{max}$ (Nujol) 1740, 1630, 1515 and 1350 cm$^{-1}$;

$\delta$ppm (CDCl$_3$) 3.46 (3H, s), 3.86 and 4.07 (2H, ABq, J 5.5 Hz, higher field arm further coupled, d, J 2.1 Hz, lower field arm further coupled, d, J 5.4 Hz), 5.03 (1H, dd, J 5.4 and 2.1 Hz), 5.14 (2H, s), 7.03 and 7.33 (4H, ABq, J 10 Hz), 7.93 and 8.26 (4H, d, J 9 Hz),8.62 (1H, s); (Found: C, 60.9; H, 4.9; N, 11.9; C$_{18}$H$_{17}$N$_3$O$_5$ requires C, 60.8; H, 4.8; N, 11.8%).

EXAMPLE 7

(3RS)-1-(p-Methoxymethoxyphenyl)-3-methylthio-3-N-p-nitrobenzylideneamino-azetidin-2-one (8)

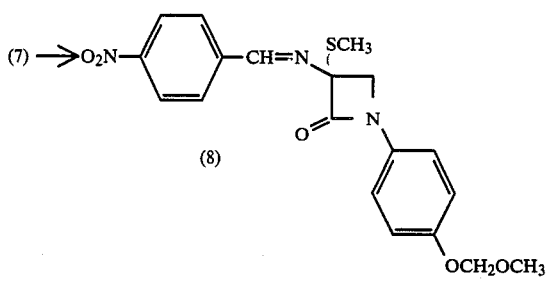

A solution of 3RS-1-(p-methoxymethoxyphenyl)-3-N-p-nitrobenzylideneamino-azetidin-2-one (7) (5.50 g) in dry dimethylformamide (75 ml) under argon was cooled to 0° C. and treated with anhydrous potassium carbonate (2.24 g). The mixture was stirred for 10 minutes, then treated with a solution of methyl methanethiosulphonate (2.05 g) in dry dimethylformamide (10 ml). The mixture was stirred at 0° C. for a ½ hour, then allowed to warm to 20° C. After 4 hours the mixture was partitioned between water and ethyl acetate. The organic phase was separated and retained. The aqueous phase was extracted with a further portion of ethyl acetate. The combined organic extractes were washed with water (x3), then brine. The solution was dried (M$_g$SO$_4$), filtered and the solvent evaporated. The residue was chromatographed on silica gel yielding an oil, which on trituration with ether gave the product (8) as a yellow crystalline solid, (3.74 g), m.p. 89°–90° C.; $\nu_{max}$ (CHCl$_3$) 1750, 1630, 1510, 1345 cm$^{-1}$; $\delta$ppm (CDCl$_3$) (90 MHz) 2.25 (s, 3H), 3.43 (s, 3H), 3.93 and 4.02 (ABq, 2H, J 6.0 Hz), 5.10 (s, 2H), 7.00 (d, 2H, J 9.0 Hz), 7.30 (d, 2H, J 9.0 Hz), 7.97 (d, 2H, J 9.0 Hz), 8.26 (d, 2H, J 9.0 Hz), 8.88 (s, 1H). (Found: C, 56.9; H, 4.8; N, 10.3; s, 8.3. C$_{19}$H$_{19}$N$_3$O$_5$S requires C, 56.9; H, 4.7; N, 10.5; S, 8.0%).

EXAMPLE 8

(3RS)-3-Amino-1-(p-methoxymethoxyphenyl)-3-methylthio-azetidin-2-one-p-toluenesulphonic acid salt (9)

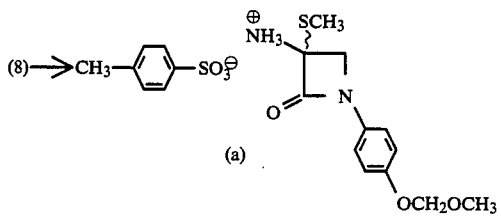

(3RS)-1-(p-Methoxymethoxyphenyl)-3-methylthio-3-N-p-nitrobenzylideneamino-azetidin-2-one (8) (3.24 g) in acetone (75 ml) was treated with a solution of 4-p-toluenesulphonic acid monohydrate (1.54 g) in acetone (30 ml). The solution was stirred vigorously. After ½ hour the precipitated salt was filtered off, washed thoroughly with ethyl acetate, then dried in vacuo, giving the product (9) (3.37 g). $\nu_{max}$ (KBr) 3415, 1745, 1515, and 1170 cm$^{-1}$; $\delta$ppm (d$_6$-DMSO) (90 MHz) 2.25 (s, 3H), 2.43 (s, 3H), 3.33 (s, 3H), 4.00 (s, 2H), 5.15 (s, 2H), 6.9 to 7.6 (m, 8H).

EXAMPLE 9

(3RS)-3-[D-2-(4-Ethyl-2,3-dioxopiperazin-1-yl-carboxamido)-2-phenylacetamido]-3-(p-methoxymethoxyphenyl)-3-methylthio-azetidin-2-one (10)

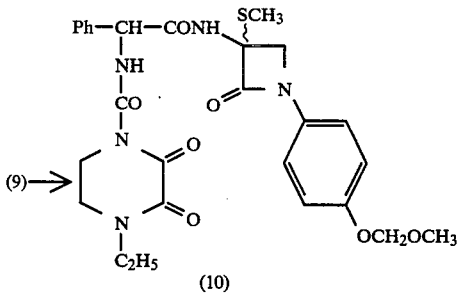

A solution of (9) (200 mg) in dry dichloromethane (10 ml), containing triethylamine (51 mg) and ground activated 4A molecular sieves (600 mg) was cooled to 0° C. and treated dropwise with a solution of 2-(4-ethyl-2,3-dioxopiperazin-1-yl-carboxamido)-2-phenylacetylchloride (184 mg) in dry dichloromethane. On completion of the addition the stirred mixture was allowed to warm to 20° C. After 2 h the mixture was filtered through Kieselguhr. The filtrate was washed successively with water, dilute HCl, water, saturated aqueous NaHCO$_3$ water, and brine, then dried (MgSO₄), filtered and the filtrate evaporated. The residue was chromatographed on silica gel to yield the product (10) (180 mg) as a ca:2:1 mixture of diastereoisomers at C(3). $\nu_{max}$(CHCl₃) 3275, 1755, 1710, 1690 cm⁻¹; δppm (CDCl₃) (250M Hz) 1.22 (t, 3H, J 6.6 Hz), 2.03 (s, 2H), 2.27 (s, 1H), 3.46 and 3.48 (both s, together 3H), 3.49 to 3.65 (m, 4H), 3.72 to 4.22 (m, 4H), 5.13 and 5.14 (both s, together 2H), 5.50 and 5.52 (both d, together 1H, both J 6.6 Hz), 6.95 to 7.55 (m, 10H), 9.88 (d, ⅓H, J 6.6 Hz), 9.96 (d, 2/3 H, J 6.6 Hz).

EXAMPLE 10

(3RS)-3-[D-2-(4-Ethyl-2,3-dioxopiperazin-1-yl-carbox-amido)-2-phenylacetamido]-3-methylthio-azetidin-2-one (11)

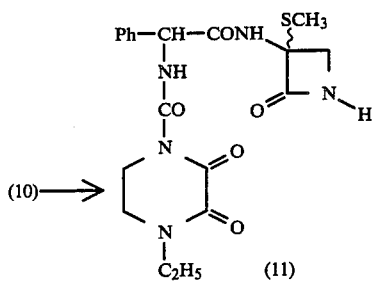

A solution of (10) (100 mg) in tetrahydrofuran 2 ml) at 0° C. was treated with ammonium ceric nitrate (CAN) (289 mg) in water (1 ml). The solution was stirred at 0° C. for 15 minutes. The cooling bath was removed and the solution treated with sodium sulphite to discharge the orange colour. The solution was poured into a vigorously stirred mixture of saturated aqueous NaHCO₃ and dichloromethane. The mixture was filtered through Kieselguhr. The organic phase of the filtrate was separated and washed with water and brine, then dried (MgSO₄), filtered and the solvent evaporated off. Chromatography of the residue on silica gel gave the product (11) (49 mg), as a white solid; a mixture of diastereoisomers at C(3) partially separable by chromatography. $\nu_{max}$ (CHCl₃) 3280, 1765, 1715, and 1690 cm⁻¹;

DIASTEREOISOMER I; δppm (CD₃OD) (250 MHz) 1.20 (t, 3H, J 6.6 Hz), 2.21 (s, 3H), 3.34 and 3.63 (ABq, together 2H, J 6.6 Hz), 3.52 (q, 2H, J 6.6 Hz), 3.59 to 3.68 (m, 2H), 3.93 to 4.14 (m, 2H), 5.51 (s, 1H), and 7.28 to 7.52 (m, 5H).

DIASTEREOISOMER II; δppm (CD₃OD) (250 MHz) 1.20 (t, 3H, J 6.6 Hz), 2.01 (s, 3H), 3.34 and 3.67 (ABq, together 2H, J 6.6 Hz), 3.51 (q, 2H, J 6.6 Hz), 3.58 to 3.67 (m, 2H), 3.91 to 4.12 (m, 2H), 5.51 (s, 1H), and 7.30 to 7.53 (m, 5H).

EXAMPLE 11

(3RS)-3-[D-2-(4-Ethyl-2,3-dioxopiperazin-1-yl-carbox-amido)-2-phenylacetamido]-3-methylsulphinyl-azeti-din-2-one (12)

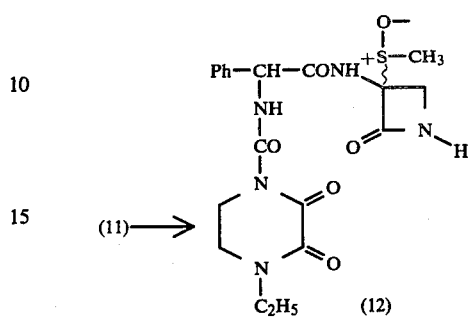

A solution of (11) (514 mg) in dry dioxan (35 ml) was treated with a solution of peracetic acid in glacial acetic acid (2.51 ml of a 5.0% w/v solution). The mixture was stirred at 20° C. for 20 min, then evaporated to dryness. The residue was evaporated twice more from dry dioxan before drying thoroughly in-vacuo. The crude product (12) (3:5 ratio of diastereoisomers at C-(3)) was used without any further purification.

$\nu_{max}$(CHCl₃) 3275, 1780, 1715 and 1690 cm⁻¹; δppm (CDCl₃) (250 MHz) 1.20 (t, 3H, J 6.9 Hz), 2.43 (s, ⅖ 3H), 2.61 (s, ⅗ 3H), 3.40 to 3.62 (m, 4H), 3.80 to 3.95 (m, 2H), 3.95 to 4.15 (m, 2H), 5.55 (d, ⅖H, J 7.0 Hz), 5.59 (d, ⅗H, J 7.0 Hz), 6.90 (s, ⅖ H), 6.95 (s, ⅗H), 7.30 to 7.55 (m, 5H), 7.77 (s, ⅖H), 8.02 (s, ⅗H), and 9.89 and 9.92 (both d, together 1H, both J 7.0 Hz).

EXAMPLE 12

(3RS)-3-Amino-3-[D-2-(4-ethyl-2,3-dioxopiperazin-1-yl-carboxamido)-2-phenylacetamido]-azetidin-2-one (13)

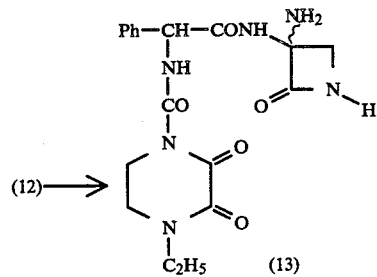

The sulphoxide (12) (489 mg) [the product of example 11] was suspended in dry tetrahydrofuran (25 ml), and dry dioxan was added to obtain a solution. The flask was fitted with a septum cap and then partially evacuated. Ammonia gas (54 ml) was injected into the flask. The mixture was stirred over night. The mixture was evaporated to dryness and the residue dried in vacuo. Chromatography of the residue on silica gel yielded the product (13), (377 mg) as a white amorphous solid, being approximately a 2:3 ratio of diastereoisomers at C(3).

$\nu_{max}$(CHCl₃) 3290, 1770, 1720, and 1690 cm⁻¹; δppm ((CD₃)₂CO) (250 MHz) 1.17 (t, 3H, J 6.6 Hz), 2.51 and 2.57 (both broad s, together 2H, exchange D₂O), 3.29 and 3.56 (ABq, minor isomer, J~5.0 Hz), 3.34 and 3.44

(ABq, major isomer, J~5.0 Hz), 3.50 (q, 2H, J~6.6 Hz, collapses to s on irradiation at 1.17), 3.63 to 3.79 (m, 2H), 3.93 to 4.15 (m, 2H), 5.60 (major isomer) and 5.62 (minor isomer) both d, together 1H, both J~8.8 Hz, both collapse to s on D$_2$O exchange), 7.17 (s, 3/5 H, exchange D$_2$O), 7.22 (s, 2/5 H, exchange D$_2$O), 7.27 to 7.57 (m, 5H), 8.16 (s, 2/5 H, exchange D$_2$O), 8.29 (s, 3/5 H, exchange D$_2$O), and 9.96 (d, 1H, J~8.8 Hz, exchange D$_2$O).

EXAMPLE 13

(3RS)-3-[D-2-(4-Ethyl-2,3-dioxopiperazin-1yl-carboxamido)-2-phenylacetamido]-3-formamido-azetidin-2-one (14)

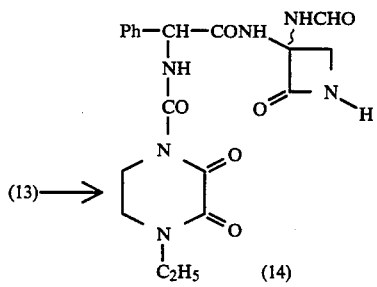

A solution of (13) (219 mg) in dry dichloromethane (4ml) containing pyridine (95 mg) at 0° C. was treated with formic-acetic anhydride (53 mg). After 30 mins at 0° C. the mixture was diluted with dry dioxan (5 ml). The solvent was evaporated off and the residue evaporated once more from dry dioxan, finally drying the residue in vacuo. Chromatography of the residue on silica gel yielded the product (14) as a white foam (quantitative), which was a mixture of diastereoisomers at C-(3).

$v_{max}$(CHCl$_3$) 3275, 1775, 1715 and 1690 cm$^{-1}$; δppm ((CD$_3$)$_2$CO) (250 MHz) 1.18 (t, 3H, J 6.0 Hz), 3.51 (q, 2H, J~6.0 Hz), 3.57 to 3.82 (m, 4H), 3.95 to 4.15 (m, 2H), 5.64 (minor isomer) and 5.66 (major isomer) (both d, together 1H, both J~7.8 Hz, both collapse to s on D$_2$O exchange), 7.26 to 7.67 (m, 6H, becomes m, 5H on D$_2$O exchange) 8.05 to 8.95 (m, 3H, becomes m, 1H at 8.06 to 8.49 on D$_2$O exchange) and, 9.94 (minor isomer) and 9.97 (major isomer) (both d, together 1H, both J~7.8 Hz, both exchange D$_2$O).

EXAMPLE 14

(3RS)-Potassium-3-[D-2-(4-Ethyl-2,3-dioxopiperazin-1-yl-carboxamido)-2-phenylacetamido]-3-formamido-2oxoazetidine-1-sulphonate (15)

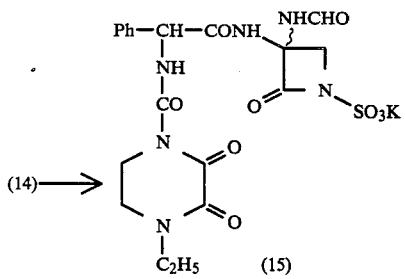

A solution of (14) (29 mg) is dry dioxan (1 ml) was treated with sulphur trioxide-pyridine complex (22 mg). The mixture was allowed to stand at room temperature for 4 days. The mixture was diluted with anhydrous ether and the precipitated solid triturated with anhydrous ether (x2). The solid was air dried, taken up in water and passed down a column of Amberlite IR-120 (K+) ion exchange resin followed by chromatography on HP20-SS to give the product, (15), as a solid (4 mg) which was a 4:5 ratio of diastereoisomers at C-(3).

$v_{max}$ (KBr) 3280, 1770, 1710, 1675, 1250, and 1050 cm$^{-1}$; δppm (D$_2$O) (250 MHz) 1.18 (t, 3H, J 6.6 Hz), 3.50 (q, 2H, J 6.6 Hz), 3.60 to 3.80 (m, 2H), 3.90 to 4.12 (m, 4H), 5.48 (s, 1H), 7.47 (broad s, 5H), 8.07 (s, 4/9H), and 8.10 (s, 5/9H).

EXAMPLE 15

(3RS)-Potassium 3-[D-2-(4-Ethyl-2,3-dioxopiperazin-1-ylcarboxamido)-2-pheylacetamido]-3-methylthio-2-oxo-azetidine-1-sulphonate (16)

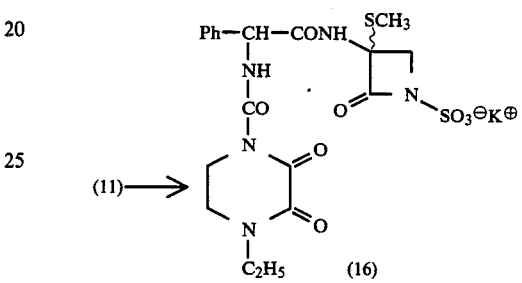

A solution of (11) (50 mg) in dry dimethylformamide (0.5 ml) under an inert dry atmoshphere was treated with pyridine-sulphur trioxide complex (37 mg). After 4 days at 20° C., ether (~4 ml) was added. The deposited solid was triturated twice with anhydrous ether then air dried. The solid was taken up in water and passed down a column of Amberlite IR 120 (K+) ion exchange resin. Chromatography on HP20 SS, and evaporation of the relevant fractions yielded the product (16), 25 mg, as a white solid being a 2:1 mixture of diastereoisomers at C-(3).

$v_{max}$ (KBr) 3290, 1765, 1710, 1675, 1245, and 1050 cm$^{-1}$; δppm (D$_2$O) (250 MHz) 1.17 (t, 3H, J 7.1 Hz), 2.06 (s,2H), 2.10 (s, 1H), 3.50 (q, 2H, J 7.1 Hz, collapse to s on irradiation at 1.17), 3.60 to 3.80 (m, 3H), 3.90 to 4.13 (m, 3H), 5.48 (minor isomer) and 5.50 (major isomer) (both s, together 1H), and 7.47 (broad s, 5H).

EXAMPLE 16

(3S)-3-Triphenylmethylaminoazetidin-2-one (18)

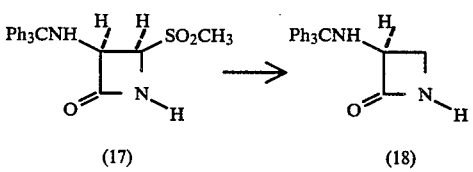

The sulphone (17) (20.3 g) (E G Brain et al. J C S Perkin Trans 1. 1976, p447) was dissolved in tetrahydrofuran (200 ml), cooled to 0° C. under argon and sodium borohydride (3.8 g) in water (36 ml) added in four portions over 10 mins. The reaction was removed from the cooling bath, allowed to warm to room temperature over 1.5 hour and glacial acetic acid (5.72 ml) added. After 15 mins the solution was diluted with ethyl acetate (600 ml), washed with water (×2), saturated sodium hydrogencarbonate solution, brine, dried (MgSO$_4$) and evaporated. Chromatography on silica gel gave the product (17) as a white crystalline solid (14.3 g). m.p. 103°–105° (toluene); $[\alpha]^{23}$ D-51.2° (c 1 CHCl$_3$); $\nu_{max}$ (Nujol) 3340, 3250, 1760, 1730 cm$^{-1}$; δppm (CDCl$_3$) 2.14 (1H, dd, J 5.9+2.4 Hz), 2.53 (1H, d, J 10.8 Hz, exchange), 2.63 (1H, dd, J 5.9 and 4.7 Hz), 4.21 (1H, broad s, collapses to dd, J 4.7 and 2.4 Hz on exchange), 5.53 (1H, broad s, exchange), 7.2–7.6 (15H, m). (Found: C, 81.3; H, 6.2; N, 7.8; C$_{22}$H$_{20}$N$_2$O. ⅛C$_7$H$_8$ requires C, 81.5; H, 6.3; N, 7.8%).

EXAMPLE 17

(3S)-1-t-Butyldimethylsilyl-3-triphenylmethylamino-azetidin-2-one (19)

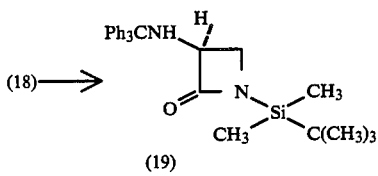

The azetidinone (328 mg) was dissolved in dry dimethylformamide (3 ml) containing t-butyldimethylchlorosilane (166 mg) at 0° C. and triethylamine (0.154 ml) in dry dimethylformamide (0.5 ml) added over 1 min. After 15 mins at 0° C. and warming to room temperature, the reaction diluted with ethyl acetate, washed with water, very dilute hydrochloric acid, brine, dried (MgSO$_4$) and evaporated. Chromatography on silica gel afforded the product (19) as a white crystalline solid (338 mg). m.p. 166° (hexane); $[\alpha]^{19}$D-56°; (c2 in CHCl$_3$) $\nu_{max}$ (KBr) 3460, 1745 cm$^{-1}$; δppm (CDCl$_3$) 0.11 (6H, s), 0.86 (9H, s), 2.21 and 2.60 (2H, ABq, d, J 6 Hz, higher field arm further coupled, d, J 2.5 Hz, lower field arm further coupled, d, J 5 Hz), 2.5–2.8 (1H, broad s, exchange), 4.20 (1H, m), 7.1–7.6 (15H, m). (Found: C, 76.1; H, 7.5; N, 6.3; C$_{28}$H$_{34}$N$_2$OSi requires C, 76.0; H, 7.7; N, 6.3%).

EXAMPLE 18

(3S)-3-Amino-1-t-butyldimethylsilyl azetidin-2-one (20)

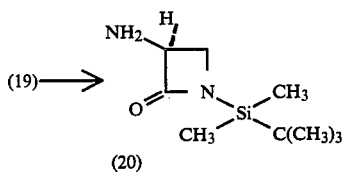

The β-lactam (277 mg) was dissolved in anhydrous dichloromethane (4 ml), cooled to 0° C. and p-toluenesulphonic acid monohydrate (119 mg) in the minimum volume of methanol was added. After 17 hours at 5° C., triethylamine (0.1 ml) was added and after 10 mins the solvent was evaporated off. Chromatography on silica gel afforded the amine (20) as a solid (66 mg) $\nu_{max}$ (CHCl$_3$) 3375, 1730 cm$^{-1}$; δppm (CDCl$_3$) 0.23 (6H, s), 0.95 (9H, s), 1.74 (2H, s, exchange) 2.97 (1H, dd, J 6.3 and 3 Hz), 3.51 (1H, dd, J 6.3 and 6 Hz), 4.24 (1H, dd, J 6 and 3 Hz). (Found: M$^+$—H, 199.1281, C$_9$H$_{19}$N$_2$OSi requires M—H$^7$ 199.1301).

EXAMPLE 19

(3S)-1-t-Butyldimethylsilyl-3-N-p-nitrobenzylideneamino azetidin-2-one (21)

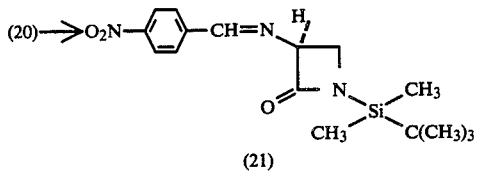

The amine (20) (2.096 g) was dissolved in toluene (50 ml) and p-nitrobenzaldehyde (1.58 g) added. The solution was vigorously stirred for 18 hours in the presence of 3A molecular sieves. The mixture was filtered through Kieselguhr and the filtrate evaporated. The residue slowly crystallised and was recrystallised from hexane to provide (21) (3.26 g); $[\alpha]^{19}$D-205° (c 0.8 in CHCl$_3$) $\nu_{max}$(CHCl$_3$) 1740, 1635, 1520, and 1350 cm$^{-1}$; δ(CDCl$_3$) 0.99 (9H, s), 3.47 (1H, dd, J 6.5 and 3 Hz), 3.68 (1H, dd, J 6.5 and 6 Hz), 5.0 (1H, m), 7.92 (2H, s, J 8 Hz), 8.28 (2H, s, J 8 Hz), and 8.55 (1H, slightly broadened s, J ca 0.5 Hz).

EXAMPLE 20

1-t-Butyldimethylsilyl-3-methylthio-3-N-p-nitrobenzylideneamino-azetidin-2-one (22)

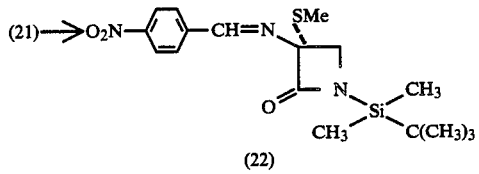

The Schiff base (21) (2.07 g) was dissolved in dry dichloromethane (45 ml) and methylmethanethiosulphonate (861 mg) added in dichloromethane (2 ml), followed by 1,5-diazabicyclo[5.4.0]undec-5-ene (1.08 g) in dichloromethane (3 ml). After 30 mins the solution was washed with aqueous ammonium chloride (×3), brine, dried, and evaporated. Chromatography on silica eluting with dichloromethane-hexane mixtures afforded the product (22) (1.33 g). m.p. 127°–128° C. $\nu_{max}$ (CHCl$_3$) 1735, 1625, 1525, and 1350 cm$^{-1}$; δ(CDCl$_3$) 0.25 (3H, s), 0.28 (3H, s), 0.98 (9H, s), 2.18 (3H, s), 3.58 (2H, ABq, J 7 Hz), 7.97 (2H, d, J 9 Hz), 8.25 (2H, d, J 9 Hz), and 8.8 (1H, s).

EXAMPLE 21

(3RS)-3-Amino-1-t-butyldimethylsilyl-3-methylthio-azetidin-2-one-p-toluenesulphonic acid salt (23)

A solution of (22) (3.32 g) in ethyl acetate (65 ml) was treated with p-toluenesulphonic acid monohydrate (1.66 g) in a minimum volume of ethyl acetate. After 15 mins the precipitate was filtered off, washed with ethyl acetate then ether and dried in vacuo, giving the product (23) (3.57 g).

$\nu_{max}$ (nujol) 3160, 1720 and 1170 cm$^{-1}$; δppm ((CD$_3$)SO) (60 MHZ) 0.20(S, 3H), 0.25 (s, 3H) 0.95 (S, 9H), 2.30 (S, 3H), 2.35 (S, 3H), 3.45 and 3.65 (ABq, 2H, J 7 Hz), 7.15 and 7.55 (ABq, 4H, J 8 Hz), 9.35 (Broad s, approx. 3H, exch). (Found: C, 48.91; H, 6.96; N, 6.80; S, 15.43. $C_{17}H_{30}N_2O_4SiS_2$ requires C, 48.77; H, 7.22; N, 6.69; S, 15.32).

EXAMPLE 22

(3RS)-1-t-Butyldimethylsilyl-3-methylthio-3-phenoxyacetamido-azetidin-2-one (24)

A suspension of (23) (830mg) in dry dichloromethane (20 ml) at $-10°$ C. was treated with triethylamine (220 mg) and pyridine (172 mg), followed by a solution of phenoxyacetyl chloride (372 mg) in dry dichloromethane ($\sim 4$ ml). The mixture was washed with very dilute HCl, followed by brine. The organic phase was dried and the solvent evaporated. Chromatography on silica yet gave the product (24) (730 mg). $\nu_{max}$(CHCL$_3$) 3400, 1745, and 1690 cm$^{-1}$; $\delta$ppm (CDCl$_3$) (90 MHz) 0.25 and 0.27 (boths, together 6H), 0.98 (S, 9H), 2.22 (S, 3H), 3.36 and 3.81 (ABq, 2H, J 7.0 Hz), 4.50 (S, 2H), 6.80 to 7.50 (m, 6H).

EXAMPLE 23

(3RS)-3-Methylthio-3-phenoxyacetamido-azetidin-2-one (25)

A solution of (24) (516 mg) in dry tetrahydrofuran (THF) (10 ml) was cooled to $-10°$ C. and treated with tetrabutylammonium fluoride (476 mg) and glacial acetic acid (180 mg) in a minimum volume of dry THF. After approximately 15 mins the mixture was poured into a mixture of ethyl acetate and water. The organic phase was separated and washed successively with dilute sodium bicarbonate, dilute hydrochloric acid, and brine, then dried and evaporated.

Chromatography on silica gel gave the product (25) (366 mg), a white solid. $\nu_{max}$ 3410, 1775 and 1690 cm$^{-1}$; $\delta$ppm (CDCl$_3$) (90 MHz) 2.24 (s, 3H), 3.48 and 3.90 (ABq, 2H, J 7.0 Hz), 4.50 (s, 2H), 6.24 (s, 1H, exch.), 6.80 to 7.45 (m, 6H, becomes m, 5H, on exch.)

EXAMPLE 24

(3RS)-3-Methylsulphinyl-3-phenoxyacetamido-azetidin-2-one (26)

A solution of (25) (175 mg) in dry dioxan (7 ml) was treated with a solution of peracetic acid in glacial acetic acid (0.99 ml of a 5.07 % w/v solution). The mixture was stirred at room temperature for approximately 20 mins, then evaporated to dryness. The residue was evaporated once more from dry dioxan before drying thoroughly in vacuo. The residue was taken up in chloroform and chromatographed on a short column of silica gel eluting with 10% meOH/CHCl$_3$ to give the product (26) (186 mg) a mixture of sulphoxide isomers (approximately 1:2) $\nu_{max}$ (CHCl$_3$) 3410, 1785, 1690, and 1490 cm$^{-1}$; $\delta$ppm (CDCl$_3$) (90 MHz) 2.60 (major isomer) and 2.67 (minor isomer) (both s, together 3H), 3.79 and 4.12 (ABq, minor isomer, J 8 Hz) and 3.87 and 4.01 (ABq, major isomer, J 6 Hz) (together 2H), 4.53 (minor isomer) and 4.60 (major isomer) both s, together 2H), 6.52 (s, 1H, exch.), 6.80 to 7.45 (m, 5H), 7.78 (s, 1H, exch.).

EXAMPLE 25

(3RS)-3-Amino-3-phenoxyacetamido-azetidin-2-one (27)

The sulphoxide (26) (186 mg) in dry tetrahydrofuran (6 ml) was treated with dry ammonia gas (14.8 ml) and the mixture stirred at room temperature for 3 days. The solvent was evaporated and the residue chromatographed on silica gel to give the product, (27) (113 mg).

$\Xi_{max}$ (CHCl$_3$) 3405, 3290, 1775, and 1680 cm$^{-1}$; $\delta$ppm (CDCl$_3$) (90 MHz) 2.29 (s, 2H, exch.), 3.49 and 3.73 (ABq, 2H, J 6 Hz), 4.43 (S, 2H), 6.34 (S, 1H, exch.), 6.8 to 7.4 (m, 5H), 7.41 (S, 1H, exch.)

EXAMPLE 26

(3RS)-3-Formamido-3-phenoxyacetamido-azetidin-2-one (28)

The amine (27) (66 mg) in dry dichloromethane (5 ml) was cooled to 0° and treated with pyridine (49 mg) followed by formic-acetic anhydride (27 mg). The mixture was stirred at 0° for 15 minutes then allowed to warm to room temperature over 15 minutes, and evaporated to dryness. The residue was chromatographed on silica gel to give the product (28) (53 mg).

$\nu_{max}$ (KBr) 3240, 1765, 1690 and 1660 cm$^{-1}$; $\delta$ppm ((CD$_3$)$_2$CO) (250 MHz) 3.81 (s, 2H), 4.57 (s, 2H), 6.90 to 7.05 (m, 3H), 7.25 to 7.37 (m, 2H), 7.40 and 7.62 (both broad s, together 1H, exch.) 7.85 to 8.60 (m, 3H, exch. to give m, 1H).

EXAMPLE 27

(3RS)-Potassium 3-Formamido-3-phenoxyacetamido-2-oxo-azetidine-1-sulphonate (29)

The $\beta$-lactam (28) (50 mg) was dissolved in warm dry dioxan (3 ml). The solution was treated with pyridine-sulphur trioxide complex (61 mg) at room temperature and stirred for approximately 72 hours. The mixture was evaporated to dryness. The residue was dissolved in water and chromatographed on "Amberlite" IR120 (K+form) ion exchange resin. The eluant was concentrated and chromatographed on Dianion HP20SS resin to give the product (29) (17 mg).

$\nu$max (KBr) 3270, 1770, 1675, 1240 and 1050 cm$^{-1}$; $\delta$ppm (D$_2$O) (250 MHz) 4.07 (AA$^1$, 2H), 4.78 (s, 2H), 6.95 to 7.45 (m, 5H), 8.14 (s, 1H).

EXAMPLE 28

(3RS)-3-Benzyloxycarbonylamino-1-t-butyldimethylsilyl-3-methylthio-azetidin-2-one (30)

A suspension of (22) (3.57 g) in dichloromethane (110 ml) at 0° was treated with triethylamine (0.873 g). Propylene oxide (70 ml) was added followed by benzyl chloroformate (1.64 g). The mixture was stirred overnight at room temperature, the solvent then evaporated and the residue dissolved in ethyl acetate. The solution was washed successively with dilute citric acid, water, dilute sodium bicarbonate solution, water and brine, then dried (MgSO$_4$), filtered and the solvent evaporated. Chromatography on silica gel yielded the product (30) (2.95 g), mp 74°–75°, $\nu_{max}$(CHCl$_3$) 3410, 1730 br, cm$^{-1}$; $\delta$ppm (CDCl$_3$) (90 MHz) 0.95 (s, 9H), 2.29 (s, 3H), 3.31 and 3.72 (ABq, 2H, J 7 Hz), 5.11 (S, 2H), 5.57 (s, 1H), 7.32 (s, 5H —Si(CH$_3$)$_2$ obscured by TMS) (Found: C 56.7; H, 7.4; N, 7.3; S, 8.2; $C_{18}H_{28}N_2O_3SSi$ requires C, 56.8; H, 7.4; N, 7.4; S, 8.4%).

EXAMPLE 29

(3RS)-3-Benzyloxycarbonyamino-3-methylthio-azetidin-2-one (31)

(30) (2.957 g) was reacted as in Example 23 to give the title compound (31) (1.846 g), as a white solid. $\nu$max (CHCl$_3$) 3420, 1775 and 1730 cm$^{-1}$; $\delta$ppm (CDCl$_3$) (90

MHz) 2.33 (s, 3H), 3.42 and 3.83 (ABq, 2H J 6.0 Hz), 5.11 (s, 2H), 5.60 (broads, 1H), 5.82 (broad s, 1H), 7.32 (s, 5H).

EXAMPLE 30

(3RS)-3-Benzyloxycarbonylamino-3-methylsulphinyl-azetidin-2-one (32)

(31) (1.836 g) was reacted as in Example 24 to give the title compound (32) (1.72 g), as a mixture of isomers (approximately 1:1) $\nu_{max}$ (Nujol) 3200, 1775, 1720, and 1020 cm$^{-1}$; δppm ((CD$_3$)$_2$SO) (90 MHz) 2.53 (s, 1½H), 2.68 (s, 1½H) 3.48 and 3.63 (ABq, 1H, J 7.0 Hz), 3.66 (s, 1H), 5.03 (s, 2H), 7.33 (s, 5H), 8.50 (broad s, 1H, exch.), 8.63 (broads, ½H, exch.), 9.04 (broads, ½H, exch.).

EXAMPLE 31

(3RS)-3-Amino-3-benzyloxycarbonylamino-azetidin-2-one (33)

(32) (1.71 g) was reacted as in Example 25 to give the title compound (33) (1.32 g) as a white solid. $\nu_{max}$ (nujol) 3400, 3260, 1760, 1735, and 1700 cm$^{-1}$; δppm ((CD$_3$)$_2$SO) (90 MHz) 3.10 and 3.40 (ABq, 2H, J 5.0 Hz), 5.01 (s, 2H), 7.33 (s, 5H), 7.72 (s, 1H, exch.), 7.91 (s, 1H, exch.).

EXAMPLE 32

(3RS)-3-Benzyloxycarbonylamino-3-formamido-azetidin-2-one (34)

(33) (1.32 g) was reacted as in Example 26 to give the title compound (34) (1.41 g) a white solid. $\nu_{max}$ (Nujol) 3330, 3225, 1775, 1730 (sh), 1720, 1660 and 1645 cm$^{-1}$; δppm ((CD$_3$)SO) (90 MHz) 3.47 and 3.52 (both s, together 2H), 5.03 (s, 2H), 7.33 (s, 5H), 7.85 to 9.00 (m, 4H, becomes m, 1H, on exch.).

EXAMPLE 33

(3RS)-Tetra-n-butylammonium 3-Benzyloxycarbonylamino-3-formamido-2-oxo-azetidine-1-sulphonate (35)

A solution of (34) (526 mg) in dry dioxan (30 ml) was treated with pyridine-sulphur trioxide complex (637 mg) and stirred at room temperature for approximately 1 hour. The mixture was evaporated and the residue dissolved in 0.5M KH$_2$PO$_4$ (25 ml). The solution was extracted with dichloromethane (×2). Tetra-n-butylammonium hydrogen sulphate (679 mg) was added to the aqueous solution, followed by extraction with dichloromethane (×4). The latter organic extracts were combined, dried and evaporated to give the product (35) (1.026 g) as a white foam. $\nu_{max}$ (CHCl$_3$) 3400, 1780, 1730, 1700 and 1050 cm$^{-1}$; δppm ((CD$_3$)$_2$CO) (90 MHz) 0.96 (t, 12H, J 7.0 Hz), 1.15 to 1.95 (m, 16H), 3.25 to 3.95 (m, 10H), 5.10 (s, 2H), 7.34 (s, 5H) 7.66 (broads, 1H) 8.15 (s, 1H).

EXAMPLE 34

(3RS)-Tetra-n-butylammonium-3-Amino-3-formamido-2-oxo-azetidine-1-Sulphonate (36)

A solution of (35) (510 mg) in methanol (20 ml) containing 10% Pd-C catalyst (150 mg) was hydrogenated at room temperature and atmospheric pressure for ½ hour. The mixture was filtered through Kieselguhr and the filtrate evaporated to dryness, giving the product (36) (412 mg; containing a trace of solvent).

$\nu_{max}$ (CHCl$_3$) 3400, 1770, 1685 and 1045 cm$^{-1}$; δppm ((CD$_3$)$_2$CO) 0.97 (t, 12H, J 7 Hz), 1.20 to 1.95 (m, 16H), 2.78 (broads, 2H, exch.), 3.25 to 3.60 (m, 9H), 3.72 (½ABq, 1H, J 6.5 Hz) 8.15 (s, 1H).

EXAMPLE 35

(3RS) Potassium 3-Formamido-3-thien-2-ylacetamido-2-oxo-azetidine-1-sulphonate (37)

Thien-2-ylacetic acid (149 mg) in dry dichloromethane (20 ml) containing one drop of dimethylformamide was treated with oxalyl chloride (159 mg). The mixture was stirred for 1 hour then evaporated to dryness. The residue was dissolved in dry acetonitrile (5 ml) and added, dropwise, to solution of (36) (391 mg) in dry acetonitrile (20 ml) containing propylene oxide (1 ml) at 0° C. After stirring for ½ hour at 0° C., cooling was removed. After 2 hour the mixture was evaporated to dryness. The residue was taken up in water (10 ml) containing a few drops of acetone and passed down a column of "Amberlite" IR120(K) ion exchange resin. Concentration of the eluant and chromatography on "Diaion" HP20SS resin eluting with water/acetone mixtures gave the product (37) (175 mg) as a white solid after freeze drying.

$\nu_{max}$ (KBr) 3490, 3270, 1775, 1675, 1245 and 1050 cm$^{-1}$; δppm (D$_2$O) (90 MHz) 3.87 (s, 2H), 4.00 (s, 2H), 6.90 to 7.10 (m, 2H), 7.28 to 7.42 (m, 1H), and 8.11 (s, 1H).

EXAMPLE 36

(3RS) Potassium 3-Formamido-3-[2,DL-thien-2-yl-2-ureidoacetamido]-2-oxo-azetidine-1-sulphonate (38)

2-Thien-2-yl-2-ureido-acetic acid (308 mg) was suspended in dry acetonitrile (5 ml) under argon at 0° C., and treated with thionyl chloride (447 mg). After 5 minutes, dry ether (10 ml) was added and the mixture stirred for a further 10 minutes. The solid was filtered off under argon and dried in vacuo. The dried solid was added to a solution of (36) (347 mg) in dry acetonitrile (10 ml) containing propylene oxide (2 ml) at 0° C. After stirring at 0° C. for 1 hour, the mixture was allowed to warm to room temperature and stirred for a further 1 hour. The mixture was evaporated to dryness and the residue taken up in water (some insoluble matter discarded). Chromatography on "Amberlite" IR120(K) ion exchange resin followed by "Diaion" HP20SS and lyophilization gave the product (38) (163 mg) as a white amorphus solid. $\nu_{max}$ (KBr) 3460, 3360, 1775, 1670, 1610 sh, 1245, and 1050 cm$^{-1}$; δppm ((CD$_3$)$_2$so) (250 MHz) 3.50 to 3.75 (m, 2H), 5.55 to 5.70 (m, 1H, simplifies on irradiation at ~6.72 ppm), 5.75 (S, 2H, exch. D$_2$O), 6.66 to 6.80 (m, 1H), 6.90 to 7.02 (m, 2H), 7.36 to 7.47 (m, 1H), 8.00 (s, ⅔H), 8.18 (d, 1/6H, J 11 Hz, becomes s on exch.), 8.31 (d, 1/6H, J 11 Hz, becomes s on exch.), 9.05 and 9.07 (both d, together ⅓H, J 11 Hz, exch. D$_2$O), 9.20 (s, ⅔H, exch. D$_2$O), 9.35 and 9.38 (boths, together ⅔H, exch. D$_2$O), 9.68 and 9.74 (both s, together ⅓H, exch. D$_2$O).

EXAMPLE 37

(3RS)-1-t-Butyldimethylsilyl-3-methylthio-3-[2-(p-nitrobenzyloxycarbonyl)-2-thien-3-ylacetamido]-azetidin-2-one (39)

A solution of (23) (418 mg) in dry dichloromethane (10 ml) containing triethylamine (222 mg) at 0° C. was treated with a solution of 2-(p-nitrobenzyloxycarbonyl)-

2-thien-3-ylacetylchloride (407 mg) in dry dichloromethane (5 ml). The mixture was stirred at 0° C. for 15 minutes, then allowed to warm to room temperature. After 1 hour the mixture was washed successively with sat.NaHCO$_3$, water, dilute HCl, water and brine. The organic phase was dried (MgSO$_4$), filtered and evaporated. Chromatography of the residue on silica gel gave the product (39) (496 mg) as a foam.

$\nu_{max}$(CHCl$_3$) 3390, 1745, 1685, 1525 and 1350 cm$^{-1}$; $\delta$ppm (CDCl$_3$) (90 MHz) 0.97 (s, 9H), 2.18 and 2.21 (boths, together 3H), 3.31 and 3.73 and, 3.33 and 3.75 (both ABq, together 2H, J 7 Hz), 4.79 and 4.81 (both s, together 1H), 5.31 (s, 2H), 7.01 (s, 1H, exch. D$_2$O), 7.10 to 7.60 (m, 5H), 8.22 (s, 2H, J 9 Hz), (—Si(CH$_3$)$_2$ obscured by TMS).

EXAMPLE 38

(3RS)-3-Methylthio-3-[2-(p-nitrobenzyloxycarbonyl)-2-thien-3-ylacetamido]-azetidin-2-one (40)

(39) (200 mg) was reacted as in Example 23 to give the title compound (40) (160 mg) as a white foam.

$\nu_{max}$ (CHCl$_3$) 3410, 1775, 1730 sh, 1690, 1525 and 1350 cm$^{-1}$; $\delta$ppm (CDCl$_3$) (90 MHz) 2.18 and 2.22 (both s, together 3H,) 3.41 and 3.83, and 3.43 and 3.80 (both ABq, together 2H, both J 6 Hz), 4.79 and 4.82 (both, together 1H), 5.29 (s, 2H), 6.01 (broad s, 1H, exch. D$_2$O), 7.05 to 7.55 (m, 6H) 8.18 (d, 2H, J 9 Hz).

EXAMPLE 39

(3RS)-3-Methylsulphinyl-3-[2-(p-nitrobenzyloxycarbonyl)-2-thien-3-ylacetamido]-azetidin-2-one (41)

(40) (120 mg) was reacted as in Example 24 to give the title compound (41) (125 mg).

$\nu$max (CHCl$_3$) 3400, 1780, 1740 sh, 1690, 1520, 1350 and 1040 cm$^{-1}$.

EXAMPLE 40

(3RS)-3-Amino-3-[2-(p-nitrobenzyloxycarbonyl)-2-thien-3-yl-acetamido]-azetidin-2-one (42)

(41) (125 mg) was reacted as in Example 25 to give the title compound (42) (69 mg).

$\nu_{max}$ (CHCl$_3$) 3400, 1775, 1740 sh, 1675, 1520, and 1345 cm$^{-1}$; $\delta$ppm ((CD$_3$)$_2$SO) (90 MHz) 2.65 (broad s, 2H, exch. D$_2$O), 3.11 and 3.33 (ABq, 2H, J 6 Hz), 5.03 (s, 1H), 5.28 and 5.30 (both s, together 2H), 7.03 to 7.25 (m, 1H), 7.34 to 7.70 (m, 4H), 7.92 and 7.98 (both s, together 1H, exch. D$_2$O), 8.18 (d, 2H, J 9 Hz), 8.73 and 8.78 (both s, together 1H, exch. D$_2$O).

EXAMPLE 41

(3RS)-3-Formamido-3-[2-(p-nitrobenzyloxycarbonyl)-2-thien-3-ylacetamido]-azetidin-2-one (43)

The amine (42) (490 mg) in dry dichloromethane was cooled to 0° C. and treated with pyridine (211 mg) followed by formic-acetic anhydride (117 mg). The mixture was stirred at 0° C. for 5 minutes then allowed to warm to room temperature. After ½ hour the solvent was evaporated and the residue dried in vacuo. The solid was triturated with dry ether, filtered off, and washed with more ether before drying in vacuo to give the product (43) (510 mg) as a white solid.

$\nu_{max}$ (NUJOL) 3250 br, 1780 sh, 1760, 1680 sh, 1655 and 1345 cm$^{-1}$.

EXAMPLE 42

(3RS)-Potassium 3-Formamido-3-[2-p-nitrobenzyloxycarbonyl)-2-thien-3-ylacetamido]-2-oxo-azetidine-1-sulphonate (44)

The $\beta$-lactam (43) (100 mg) was suspended in dry dioxan (6 ml) and treated with pyridine-sulphur trioxide (37 mg). The mixture was stirred at room temperature for 40 h, then the solvent was evaporated. The residue was taken up in water containing a small quantity of KH$_2$PO$_4$ (—some insoluble solids were discarded), and chromatographed on "Amberlite" IR120(K) ion exchange resin followed by "Diaion" HP20SS. Lyophilization gave the product (44) (30 mg) as a white amorphus solid.

$\nu_{max}$ (KBr) 3460 sh, 3300, 1775, 1745 sh, 1680, 1350 and 1050 cm$^{-1}$; $\delta$ppm (D$_2$O) (250 MHz) 3.92 (d, 1H, J 6.7 Hz), 4.01 and 4.02 (both d, together 1H, both J 6.7 Hz), 5.26 to 5.45 (m, 2H), 7.08 to 7.18 (m, 1H), 7.40 to 7.60 (m, 4H), 8.08 and 8.09 (both s, together 1H), 7.23 (d, 2H, J 8 Hz).

EXAMPLE 43

(3RS)-Dipotassium 3-(2-carboxylate-2-thien-3-ylacetamido)-3-formamido-2-oxo-azetidine-1-sulphonate (45)

A solution of (44) (70 mg) in water (5 ml) containing 10% Pd-C (35 mg) was hydrogenated at atmospheric pressure and room temperature for ½ hour. The mixture was filtered to remove the catalyst. Chromatography of the filtrate on "Amberlite" IR120(K) ion exchange resin followed by "Diaion" HP20SS and lyophilization gave the product (45) (40 mg) as a white solid.

$\nu_{max}$ (KBr) 3440, 3260, 1775, 1670, 1605 and 1050 cm$^{-1}$; $\delta$ppm (D$_2$O) (250 MHz) 3.98 to 4.14 (m, 2H), 4.67 and 4.69 (both s together 1H), 7.07 to 7.13 (m, 1H), 7.28 to 7.36 (m, 1H), 7.40 to 7.48 (m, 1H), 8.13 and 8.15 (both s, together 1H).

EXAMPLE 44

Potassium (3RS)-3-[2-Chloroacetamidothiazole-4-yl)-2-methoxyiminoacetamido]-3-formamido-2-oxo-azetidine-1-sulphonate (46)

2-(2-Chloroacetamidothiazol-4-yl)-(Z)-methoxyiminoacetyl chloride (500 mg) was suspended in dry acetonitrile (20 ml) and propylene oxide (5 ml) added to give a clear solution which was cooled to −20° C. The amine (36) (677 mg) in dry acetonitrile (5 ml) was added. After 20 minutes the solvents were evaporated and the residue dried in vacuo. The crude product was dissolved in dry acetone (2 ml) and potassium nonafluorobutane sulfonate (509 mg) added in the minimum volume of acetone. The slurry was diluted with an equal volume of ether and filtered to give the crude potassium salt. Chromatography on "Diaion" HP20SS resin eluting with water and then 7½% acetone; wateer gave the pure product (46) (501 mg) after freeze drying $\nu_{max}$ (KBr) 3450 br, 3240 br, 1775, 1675 br and, 1045 cm$^{-1}$; $\delta$ppm (D$_2$O) (250 MHz) 4.01 (s, 3H), 4.13 and 4.20 (2H, ABq, J 6.3 Hz), 4.42 (2H, s), 7.48 (1H, s), and 8.20 (1H, s).

EXAMPLE 45

Potassium (3RS)-3-[2-(2-Aminothiazol-4-yl)-2-methoxy-iminoacetamido]-3-formamido-2-oxo-azetidine-1-sulphonate (47).

The lactam (46) (100 mg) was dissolved in water (1.5 ml) at 5° C. and sodium N-methyldithiocarbamate (39 mg) added. The mixture was stirred at room temperature for 1½ hour, washed with ethyl acetate and evaporated. Chromatography on "Diaion" HP20SS resin eluting with water and freeze drying of the relevant fractions afforded (47) (46 mg). $\nu_{max}$ (KBr)3420br, 3320br, 1775, 1665, 1620sh, and 1045 cm$^{-1}$; δppm (D$_2$O) (250 MHz) 3.90 (3H, s), 4.09 (2H, s), 6.9 (1H, s), 8.15 (1H, s).

EXAMPLE 46

3-Hydroxy-2-phthalimido-N-benzyloxybutyramide (49)

Phthalimido threonine (48) (52.40 g) and —O—benzylhydroxylamine hydrochloride (47.62 g) were suspended in water (800 ml) and the pH of the solution adjusted to 4.5 (3N-NaOH), followed by the addition of N,N-dimethylformamide (200 ml). To the resulting solution was added a solution of 1-(3-dimethylaminopropyl-3-ethylcarbodiimide hydrochloride (44.30 g) in water (350 ml) whilst keeping the solution stirred and maintaining pH at 4.5 using 5N-HCl. Stirring was continued at that pH for 1 hour after addition was complete. The mixture was then extracted with ethyl acetate (4×350 ml), and the combined organic layers washed sequentially with 1N-citric acid (200 ml), 5% aqueous sodium hydrogen carbonate (100 ml) and saturated brine (100 ml), dried (MgSO$_4$) and evaporated. Silica gel chromatography of the residue gave the product (49) (59.56 g), $\nu_{max}$ (CHCl$_3$) 3400, 1770, 1710 and 1385 cm$^{-1}$; δ(CDCl$_3$) 1.18 (d, J 6.5 Hz, 3H) (irradiation at 4.59 caused this signal to collapse to a s) 4.0 br (1H, exch.), 4.52 (m, 1H) [irradiation at 1.18 caused this signal to collapse to a d (J 5 Hz)], 4.78 (d, J 5 Hz, 1H), 4.87 (s, 2H), 7.2–7.5 (m, 5H), 7.6–7.9 (m, 4H), m/e 354 (M+), and 91 (base peak.)

EXAMPLE 47

N-Benzyloxy-2-phthalimido-3-methylsulphonyloxybutyramide (50)

Methanesulphonyl chloride (19.1 ml) was added in one portion to a cooled (ice bath), stirred solution of (49) (59.62 g) in pyridine (250 ml). After 5 minutes the mixture was allowed to gradually reach room temperature. After 1 hour ethyl acetate (700 ml) was added and the mixture washed sequentially with water (2×500 ml), 1.67N-HCl (2×500 ml), and dilute aqueous sodium hydrogen carbonate. The organic layer was dried (MgSO$_4$) and evaporated to give the product as a light yellow foam (68.74 g). $\nu_{max}$ (CHCl$_3$) 3250, 1780, 1715 and 1175 cm$^{-1}$; δ(CDCl$_3$) 1.50 (d, J 6 Hz, 3H) (irradiation at 5.54 caused this signal to collapse to a s), 2.83 (s, 3H), 4.85 (d, J 8 Hz, 1H), 4.84 (s, 2H), 5.54(m, 1H), 7.1–7.4 (m, 5H), 7.6–7.9 (m, 4H), and 9.50br (1H, exch.).

EXAMPLE 48

Trans-1-Benzyloxy-4-methyl-3-phthalimidoazetidin-2-one (51)

The mesylate (50) (71.48 g) was taken up in acetone (2380 ml) under an argon atmosphere and solid potassium carbonate (68.37 g) added with stirring. The mixture was heated on an oil bath at 80° C. for 1 hour and then cooled. The solid was filtered off and filtrate concentrated. Towards the end of evaporation some ethyl acetate was added and the mixture re-concentrated, leading to the deposition of the product as a white solid. The solid was filtered off (26.60 g) and the filtrate evaporated and purified on silica gel to give a further quantity of product (6.88 g), m.p. 156° C. (from CHCl$_3$—Et$_2$O), $\nu_{max}$ (CHCl$_3$) 1800, 1780, 1710 and 1395 cm$^{-1}$, δ(CDCl$_3$) 1.25 (d, J 6 Hz, 3H), 4.02(dq J 6 and 2 Hz, 1H) [irradiation at 1.25 and 4.73 caused this signal to collapse a d (J 2 Hz) and a q (J 6 hz) respectively], 4.72 (d, J, 2 Hz, 1H) (irradiation at 4.10 caused this signal to collapse to a s), 5.10 (s, 2H), 7.2–7.6(m, 5H), and 7.6–7.9(m, 4H). (Found: C, 67.81; H, 4.73; N, 8.35. C$_{19}$H$_{16}$N$_2$O$_4$ requires C, 67.85; H, 4.79; N, 8.33%).

EXAMPLE 49

Trans-1-Hydroxy-4-methyl-3-phthalimidoazetidin-2-one (52)

The O-benzyl derivative (51) (23.08 g) was taken up in THF (250 ml) and hydrogenolysed in the presence of 10% Pd/C until no starting material remained. The solution was filtered through Kieselguhr and the filtrate evaporated to give a white solid (52) (16.63 g), m.p. 94°–96° C. (from EtoAc—hexane), $\nu_{max}$ (KBr) 3400, 1795, 1770, 1720, and 1400 cm$^{-1}$, δ(CDCl$_3$) 1.45(d, J 6.5 Hz, 3H) (irradiation at 4.18 caused this signal to collapse to a s), 4.18 (dq, j 6.5 and 2 Hz, 1H), 4.70(d, J 2 Hz, 1H) (irradiation at 4.18 caused this signal to collapse to a s), 7.3–8.0 (m, 4H), and 7.7–8.7br (1H, exch.), m/e 246(M+) and 187 (base peak). (Found: C, 58.28; H, 4.11; N, 11.46; M+246.0647. C$_{12}$H$_{10}$N$_2$O$_4$ requires C, 58.54; H, 4.09; N, 11.38%, M, 246.0681).

EXAMPLE 50

Trans-4-Methyl-3-phthalimidoazetidin-2-one (53)

A solution of the N-hydroxyazetidinone (52) (16.9 g) in methanol (480 ml) was treated with 4.5M-ammonium acetate (390 ml), followed by a 30% solution of titanium trichloride (147 ml). After stirring the above mixture for 1.5 hour the solution was concentrated in vacuo and then neutralised by the addition of solid sodium hydrogen carbonate. The resulting emulsion was extracted with ethyl acetate (×6) and the combined organic extracts dried (MgSO$_4$) and evaporated to give a cream solid (11.6 g), m.p. 214°–216° C. (from CHCl$_3$—Et$_2$O), $\nu_{max}$ (KBr) 3320, 2460, 1795, 1780, 1770, 1725, and 1705 cm$^{-1}$, δ[(CD$_3$)SO] 1.29 (d, J 6 Hz, 3H), 4.04 (dq, J6 and 2 Hz, 1H), 4.80 (d, J 2 Hz, 1H), 7.94 (s, 4H), and 8.48br(1H, exch.) (Found: C, 62.60; H, 4.44; N, 12.28. C$_{12}$H$_{10}$N$_2$O$_3$ requires C, 62.61; H, 4.38; N, 12.17%).

EXAMPLE 51

Trans-1-(tert-Butyldimethyl)silyl-4-methyl-3-phthalimido azetidin-2-one (54)

A solution of the azetidinone (53) (12.12 g) and tert-butyl dimethyl silyl chloride (8.77 g) in N,N-dimethyl formamide (120 ml) was cooled in an ice-bath and triethylamine (8.07 ml) added in portions. The solution was stirred at that temperature for 0.5 hour and then at room temperature for 3 hour. Ethyl acetate (600 ml) was added and the resulting mixture washed with ice-cold water (4×300 ml) followed by 0.5M citric acid (3×300 ml). The organic solution was dried (MgSO$_4$) and evaporated to give a residue which was chromatographed on silica gel giving the title compound (54) as a white solid (11.88 g), m.p. 165° C. (From EtOAc—Hexane), $\nu_{max.}$ (KBr) 1775, 1745, 1720, 1390, 1180, and 710 cm$^{-1}$, $\delta$[(CD$_3$)$_2$SO|(CD$_3$)$_2$CO] 0.30 (s, 6H), 1.04 (s, 9H), 1.45(d, J 6 Hz, 3H), 4.19 (dq, J 6 and 3 Hz, 1H), 4.89 (d, J 3 Hz, 1H) and 7.92 (s, 4H). (Found; C, 62.77; H, 6.82; N, 8.00. C$_{18}$H$_{24}$N$_2$O$_3$Si requires C, 62.76; H, 7.02; N, 8.13%).

EXAMPLE 52

Trans-3-Amino-1-(tert-butyldimethyl)silyl-4-methylazetidin-2-one (55)

The azetidinone (54) (11.88 g) in spectrograde chloroform (190 ml) was treated with N-methylhydrazine (4 ml) in the dark for 50 hour at room temperature. The reaction mixture was filtered and the filtrate evaporated to give a yellow syrup (55) (5.65 g), $\nu_{max.}$ (CHCl$_3$) 3370, 1735, 1725, and 1315 cm$^{-1}$, $\delta$(CDCl$_3$) 0.25 (s, 6H), 0.97 (s, 9H), 1.38 (d, J 6 Hz, 3H), 1.85br (2H), 3.43 (dq, J 6 and 2.5 Hz, 1H), and 3.67 (d, J 2.5 Hz, 1H).

EXAMPLE 53

Trans-1-(tert-Butyldimethyl)silyl-4-methyl-3-(4-nitrobenzylideneamino)azetidin-2-one (56)

A solution of 4-nitrobenzaldehyde (56) (4.00 g) in dry toluene (50 ml) was added to a solution of the azetidin one (55) (5.65 g) in dry toluene (100 ml) and the resulting solution stirred overnight in the presence of 4A molecular sieves. The reaction mixture was then filtered and filtrate evaporated to give a yellow syrup which was taken up in a little ethyl acetate. The solution was cooled in an ice-bath and hexane added to give the product (56) as a cream solid (7.60 g), m.p. 104° C. (from EtOAc—hexane), $\nu_{max.}$ (KBr) 1735, 1635, 1600, 1520, and 1340 cm$^{-1}$, $\delta$(CDCl$_3$)0.30 (s, 6H), 1.00 (s, 9H), 1.48 (d, J 6.5 Hz, 3H) (irradiation at 3.90 caused this signal to collapse to a s), 3.90 (dq, J 6.5 and 2 Hz, 1H) [irradiation at 4.40 caused this signal to collapse to a q (J 6.5 Hz)], 4.40 (m, 1H) [irradiation at 3.90 caused this signal to collapse to a d (J 1 Hz)], 7.90 and 8.25 (each d, J 8.5 Hz, 4H), and 8.47 (d, J 1 Hz, 1H) (irradiation at 4.40 caused this signal to collapse to a s). (Found: C, 59.02; H, 7.20; N, 12.08. C$_{17}$H$_{25}$N$_3$O$_3$Si requires C, 58.76; H, 7.25; N, 12.09%).

EXAMPLE 54

(Tert-Butyldimethyl)silyl-4-methyl-3-methylthio-3-(4-nitrobenzylideneamino)azetidin-2-one (57)

A solution of DBU (3.75 ml) in dry dichloromethane (50 ml) was added to a cooled (ice-bath) solution of the Schiff base (56) (7.6 g) and methyl methanethiosulphonate (2.27 ml) in dry dichloromethane (100 ml). After stirring for 30 min, the reaction mixture was diluted with more dichloromethane and washed with saturated aqueous ammonium chloride, dried (MgSO$_4$) and evaporated to give a deep yellow solid which was rapidly chromatographed on silica gel to give the product (57) as a light yellow solid (6.42 g), m.p. 118°–119° C. (from EtOAc—hexane); $\nu_{max.}$(KBr) 1720, 1625-1597, 1515, 1370, 1315, and 1195 cm$^{-1}$, $\delta$(CDCl$_3$) 0.30 and 0.33 (2s, 6H), 1.00(s, 9H), 1.30 (d, J 6.5 Hz, 3H), 2.14 (s, 3H), 3.90 (q, J 6.5 Hz, 1H) (irradiation at 1.30 caused this signal to collapse to a s), 7.98 and 8.25 (each d, J 8.5 Hz, 4H), and 8.83 (s, 1H). (Found: C, 54.99; H, 6.77; N, 11.02; S, 8.06. C$_{18}$H$_{27}$N$_2$O$_3$S Si requires C, 54.93; H, 6.91; N, 10.68, S, 8.15%).

EXAMPLE 55

3-Amino-1-(tert-butyldimethyl)silyl-4-methyl-3-methylthioazetidine-2-one, p-toluene sulphonic acid salt (58)

A solution of p-toluene sulphonic acid (82 mg) in the minimum quantity of ethyl acetate was added in one portion of the Schiff base (57) (170 mg) in ethyl acetate (3 ml). After 10 minutes the solvent was removed in vacuo. Trituration of the residue with dry ether resulted in the formation of the product as a cream solid (63 mg); m.p. 300° C. (from MeOH—Et$_2$O), $\nu_{max.}$ (KBr) 2930, 2720, 1745, 1600, 1545, 1320, 1230, 1195, 1170, 1130, 1035, and 1010 cm$^{-1}$, $\delta$[(CD$_3$)$_2$SO] 1.20 and 1.25 (each s, 6H), 1.41 (d, J 6.5 Hz, 3H), 2.34 and 2.41 (each s, 6H), 3.97 (q, J 6.5 Hz, 1H), 7.28 and 7.69 (each d, J 8 Hz, 4H), and 8.7–9.8br (3H, exch). (Found: C, 50.10; H, 7.23; N, 6.72; S, 14.84 C$_{18}$H$_{32}$N$_2$O$_4$S$_2$Si requires C, 49.97; H, 7.45; N, 6.47; S, 14.82%).

EXAMPLE 56

(Tert-Butyldimethyl)silyl-3-[2-(4-ethyl-2,3-dioxopiperazine-1-carbonylamino)-2-phenylacetamido]-4-methyl-3-methylthioazetidin-2-one (59)

A solution of the tosylate (58) (680 mg) in dry dichloromethane containing pyridine (250 mg) was cooled in an ice-bath and treated with a solution of 2-(4-ethyl-2,3-dioxopiperazine-1-carbonylamino)-2-phenylacetylchloride (750 mg) in dry dichloromethane for 30 minutes. The reaction mixture was washed successively with dilute HCl, saturated aqueous sodium hydrogen carbonate, and brine, then dried (MgSO$_4$), filtered, and the filtrate evaporated. The residue was chromatographed on silica gel to give the product (59) (420 mg) as a mixture of diastereoisomers; $\nu_{max.}$ (CHCl$_3$) 3400, 3280, 1740, 1720, and 1690 cm$^{-1}$, $\delta$(CDCl$_3$) 0.17, 0.2, 0.21, 0.23, and 0.24 (each s, together 6H), 0.95 and 0.97 (each s, together 9H), 1.05-1.29 (complex m, together 6H), 1.84, 1.86, 2.22 and 2.23 (each s, together 3H), 3.46-3.64 (m, 4H), 3.69 (2xq, J 6.5 Hz, together 1H), 3.92-4.20 (complex m, together 2H), 5.45-5.6 (complex m, 1H) (irradiation at 9.95 caused this signal to simplify to 4xs) 6.70, 6.79, 6.81 and 6.85 (each s, together 1H), 7.30-7.55 (m, together 5H), 9.86-10.02 (complex m, together 1H) [irradiation at 1.16 caused the signals at (3.92-4.20) to simplify whilst the signals centered at 3.69 collapsed to (2xs)].

EXAMPLE 57

3[2-(4-Ethyl-2,3-dioxopiperazine-1-carbonylamino)-2-phenylacetamido]-4-methyl-3-methylthioazetidin-2-one (60)

To a cooled (−20° C.) solution of the N-silylazetidinone (59) (193 mg) in tetrahydrofuran (5 ml) was added a solution of glacial acetic acid (23 mg) and tetra-N-butylammonium fluoride (119 mg) in tetrahydrofuran (2 ml) with stirring. After 15 minutes the mixture was poured into ethyl acetate (40 ml) and washed in turn with 5% citric acid and saturated brine, dried (MgSO$_4$) and evaporated to give a cream solid. Chromatography on silica gel gave the product (60) (78 mg) as an off-white solid, $\nu_{max.}$ (nujol) 3500, 3250, 1760, 1710, and 1670 cm$^{-1}$, $\delta$[(CD$_3$)$_2$SO] 0.84, 0.97, 1.13 and 1.17 (each d, J 6.5 Hz, together 3H), (irradiation at 3.56 caused the signals centered at 0.84 and 0.97 to collapse to 2xs), 1.07(t, J 7 Hz, 3H) (irradiation at 3.46 caused this signal to collapse to a s), 1.81, 1.87, and 2.08 (each s, together 3H), 3.46 (q, J 7. Hz, 2H), 3.59–4.00 (complex m, together 5H), 5.55–5.70 (complex m, together 1H) (D$_2$O exchange caused this set of signals to resolve into 2 broad s centered at 5.53 and 5.56), 7.25–7.58 (m, 5H), 8.30, 8.36, and 8.42br (each s, together 1H, exch.), 9.22 br (s, 1H, exch.), and 9.70–9.95 (m, together 1H, exch).

EXAMPLE 58

3[2-(4-Ethyl-2,3-dioxopiperazine-1-carbonylamino)-2-phenylacetamido]-4-methyl-3-methylsulphinylazetidin-2-one (61)

The azetidinone (60) (250 mg) in dry dioxan (10 ml) was treated with a (5.07% w/v) solution of peracetic acid in acetic acid (0.69 ml) for 1.5 hour. The solvent was then evaporated in vacuo, the complete removal of acidic residues being ensured. Silica gel chromatography of the residue gave the title compound as a pale-white solid (149 mg), $\nu_{max}$. (Nujol) 3300, 1760, 1710, and 1670 cm$^{-1}$, $\delta[(CD_3)_2SO]$ 0.65, 0.93, 1.16 and 1.19 (each d, J 6.5 Hz, together 3H), 1.07 (t, J 7 Hz, 3H), 1.99, 2.14, 2.39, 2.64 and 2.68 (each s, together 3H), 3.37 (q, J 7 Hz, 2H), 3.47–3.52 (m, 2H), 3.79–3.92 (m, 2H), 3.92–4.10 (complex m, together 1H), [5.45–5.60 (complex m) and 5.86 (d, J 7 Hz), together 1H], 7.27–7.55 (m, 5H), 8.63 and 8.74 br (each s, together 1H, exch), 9.14 and 9.35 br (each s, together 1H, exch.), and 9.65–10.00 (complex m, together 1H, exch).

EXAMPLE 59

3-Amino-3[2-(4-ethyl-2,3-dioxopiperazine-1-carbonylamino)-2-phenylacetamido]-4-methylazetidin-2-one (62)

The sulphoxide (61) (145 mg) in dioxan (5 ml) was treated with ammonia (21 ml) overnight at room temperature. The solvent was then evaporated and the residue chromatographed on silica gel to give the product (62) as a white solid (95 mg), $\nu_{max}$. (CHCl$_3$) 3400, 3280, 1770, 1715 and 1690 cm$^{-1}$, $\delta$ (CDCl$_3$) 0.87, 0.90, 1.10 and 1.14 (each d, J 6 Hz, together 3H), 1.20 (t, J 7 Hz, 3H), 1.6–2.9 br (2H, exch.), 3.40–3.65 (m, 4H) (irradiation at 0.90 caused this signal to simplify), 3.85 (2xq, J 7 Hz, together 1H) (irradiation at 0.87 or 1.10 caused one of the above signals to collapse to a s), 3.95–4.13(m, 2H), 5.45(2xd, J 7 Hz, together 1H, collapses to 2xs on exch), 6.50, 6.58, 6.63, and 6.72 br (each s, together 1H, exch.), 7.25–7.56 (m, 5H), 7.62, 7.76, 7.90, and 8.06 br (each s, 1H, exch.), and 9.90 (2xd, J 7 Hz, together 1H, exch.).

EXAMPLE 60

3[2-(4-Ethyl-2,3-dioxopiperazine-1-carbonylamino)-2-phenylacetamido]-3-formamido-4-methylazatidin-2-one (63)

A solution of the amine (62) (87 mg) and pyridine (33 mg) in dry dichloromethane (2 ml) was treated with formic acetic anhydride (40 mg) for 24 hour after which time the solvent was removed in vacuo. Dry dioxan was added and solution re-evaporated (×3). Silica gel column chromatography of the residue gave the title compound (63) (80 mg) as a white powder, $\nu_{max}$. (Nujol) 3500, 3250, 1770, 1710, 1670, and 1500 cm$^{-1}$, $\delta[(CD_3)_2CO]$ 0.88, 0.96, 1.00 and 1.03 (each d, J 6.5 Hz, together 3H) (irradiation at 4.00 caused the signals centered at 0.88 and 0.96 to collapse to 2 x s), 1.16 (t, J 7 Hz, 3H), 3.49(q, J 7. Hz, 2H), 3.58–3.68 (m.2H), 3.93–4.23 (complex m, together 3H), 5.59–5.84 (complex m, together 1H) (collapses to 4 x s at 5.65, 5.69, 5.76 and 5.80 upon irradiation at 10.0), 7.25–7.80 (complex m, together 6H) (simplifies on exchange with D$_2$O to a m at 7.25–7.56), 7.97–8.86 (complex m, together 3H) (simplifies to 4xs at 8.03, 8.11, 8.24, and 8.48 on exch.), 9.90–10.05 (m, 1H, exch).

EXAMPLE 61

Potassium 3[2-(4-Ethyl-2,3-dioxopiperazine-1-carbonylamino)-2-phenylacetamido]-3-formamido-4-methyl-2-oxo-azetidine-1-sulphonate (64)

The azetidinone (63) (110 mg) and sulphur trioxide-pyridine complex (200 mg) in dry dioxan (8.5 ml) were stirred for 4 days and then evaporated to dryness. The residue was taken up in a little water, passed down a column of IR120 (K+ form) ion exchange resin. The eluant was concentrated and purified on Diaion HP20SS resin to give the title compound (64) (42 mg) $\nu_{max}$. (KBr) 3500, 3300, 1775, 1710, 1685, and 1045 cm$^{-1}$, $\delta(D_2O)$ 1.0–1.3 (complex m, 6H), 3.50 (q, J 7 Hz, 2H) (irradiation at 1.20 caused this signal to collapse to a s), 3.6–3.8 (m, 2H), 3.9–4.1 (m, 2H), 4.2–4.5 (complex m, together 1H) (irradiation at 1.20 caused this signal to collapse to 3 x s at 4.26, 4.32 and 4.40), 5.4–5.6 (m, 1H) (irradiation at 9.83 caused this signal to simplify to 2 x s at 5.50 and 5.52), 7.4–7.6 (m, 5H), 8.07, 8.13 and 8.25 (each s, together 1H), and 9.7–9.9 (m, 1H).

DEMONSTRATION OF EFFECTIVENESS

In a standard microtitre (MIC) test, the compound of Example 14 gave the following data:

| Organism | MIC(μg/ml) |
| --- | --- |
| E. coli JT4 | 25 |
| E. coli NCTC 10418 | 12.5 |
| S. marcescens US32 | 12.5 |
| K. aerogenes A | 3.2 |
| E. cloacae N1 | 12.5 |
| P. morganii | 6.4 |
| S. aureus Russell | 3.2 |

We claim:
1. A compound of the Formula (I):

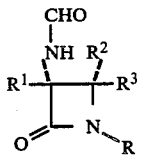

(I)

or a pharmaceutically acceptable base salt thereof wherein R is —SO$_3$H; R$^1$ is amino, t-butylcarbonylamino, benzyloxycarbonylamino or benzylideneamino, or is selected from the sub-formulae (a)–(f):

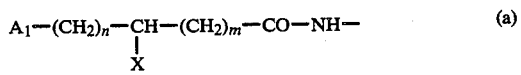

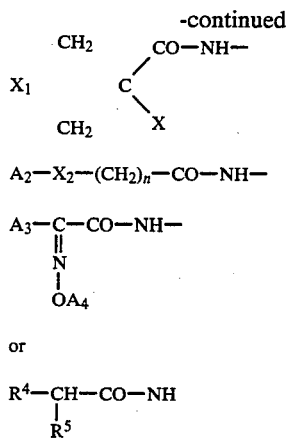

(c)

A₂—X₂—(CH₂)ₙ—CO—NH—  (d)

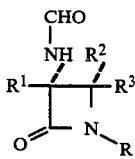

(e)

or

R⁴—CH—CO—NH  (f)
|
R⁵ wherein n is zero, one or two, m is zero, one or two; $A_1$ is alkyl of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or di-alkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; $R^4$ is a phenyl, thienyl or phenoxy group; $R^5$ is methyl; and $R^2$ and $R^3$ are independently selected from hydrogen or a hydrocarbon group of 1 to 18 carbon atoms.

2. A pharmaceutical composition useful for treating bacterial infections in humans and animals which comprises an antibacterially effective amount of a compound of the Formula (I):

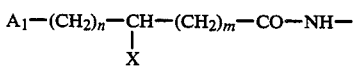

or a pharmaceutically acceptable base salt thereof wherein R is —SO₃H; $R^1$ is amino, t-butylcarbonylamino, benzyloxycarbonylamino or benzylideneamino, or is selected from the sub-formulae (a)–(f):

A₁—(CH₂)ₙ—CH—(CH₂)ₘ—CO—NH—  (a)
|
X

A₂—CO—NH—  (b)

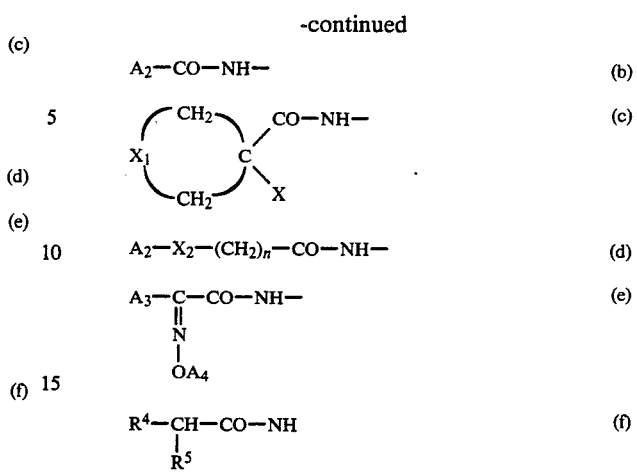

(c)

A₂—X₂—(CH₂)ₙ—CO—NH—  (d)

A₃—C—CO—NH—  (e)
‖
N
|
OA₄

R⁴—CH—CO—NH  (f)
|
R⁵ wherein n is zero, one or two, m is zero, one or two; $A_1$ is alkyl of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or di-alkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; $R^4$ is a phenyl, thienyl or phenoxy group; $R^5$ is methyl; and $R^2$ and $R^3$ are independently selected from hydrogen or a hydrocarbon group of 1 to 18 carbon atoms, in combination with a pharmaceutically acceptable carrier.

3. A pharmaceutical composition useful for treating bacterial infections in humans and animals which comprises an antibacterially effective amount of a compound of the formula (II):

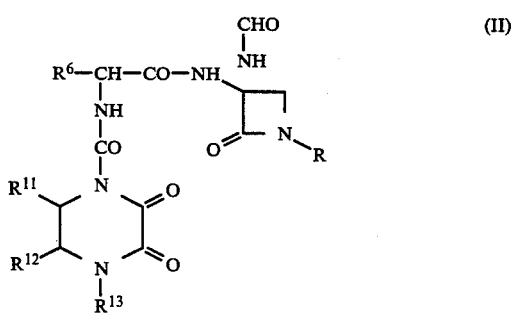

or a pharmaceutically acceptable salt thereof wherein R is —$SO_3H$; $R^6$ is phenyl, hydroxyphenyl, cyclohexadienyl, or a 5- or 6-membered heterocyclyl group containing one to three heteroatoms selected from sulphur, oxygen or nitrogen, said group being optionally substituted by one, two or three substituents selected from hydroxy, amino, halo and alkoxy; $R^{11}$ and $R^{12}$ are each hydrogen, alkyl of 1 to 6 carbon atoms, halo, amino, hydroxy or alkoxy of 1 to 6 carbon atoms; and $R^{13}$ is hydrogen, alkyl of 1 to 6 carbon atoms or benzyl, in combination with a pharmaceutically acceptable carrier.

4. A method of treating bacterial infections in humans and animals which comprises administering to a human or animal in need thereof an antibacterially effective amount of a compound of the Formula (I):

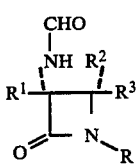
(I)

or a pharmaceutically acceptable base salt thereof wherein R is —$SO_3H$; $R^1$ is amino, t-butylcarbonylamino, benzyloxycarbonylamino or benzylideneamino, or is selected from the sub-formulae (a)-(f):

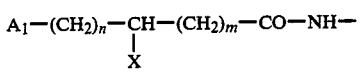
(a)

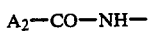
(b)

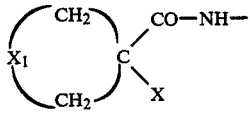
(c)

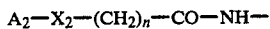
(d)

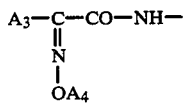
(e)

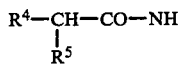
(f)

wherein n is zero, one or two, m is zero, one or two; $A_1$ is alk of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or di-alkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; $R^4$ is a phenyl, thienyl or phenoxy group; $R^5$ is methyl; and $R^2$ and $R^3$ are independently selected from hydrogen or a hydrocarbon group of 1 to 18 carbon atoms, in combination with a pharmaceutically acceptable carrier.

5. A method of treating bacterial infections in humans and animals which comprises adminstering to a human or animal in need thereof an antibacterially effective amount of a compound of the formula (II):

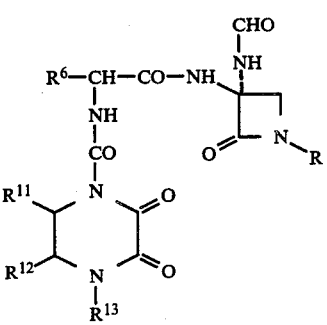
(II)

or a pharmaceutically acceptable salt thereof wherein R is —$SO_3H$; $R^6$ is phenyl, hydroxyphenyl, cyclohexadienyl, or a 5- or 6-membered heterocyclyl group containing one to three heteroatoms selected from sulphur, oxygen or nitrogen, said group being optionally substituted by one, two or three substituents selected from hydroxy, amino, halo and alkoxy; $R^{11}$ and $R^{12}$ are each hydrogen, alkyl of 1 to 6 carbon atoms, halo, amino, hydroxy or alkoxy of 1 to 6 carbon atoms; and $R^{13}$ is hydrogen, alkyl of 1 to 6 carbon atoms or benzyl, in combination with a pharmaceutically acceptable carrier.

6. A compound according to claim 1 wherein $R^1$ is amino, t-butoxycarbonylamino, benzyloxycarbonylamino or benzylideneamino.

7. A compound according to claim 1 wherein $R^1$ is of the sub-formulae (a)–(e):

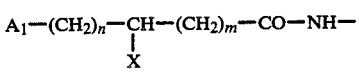
(a)

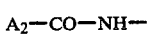
(b)

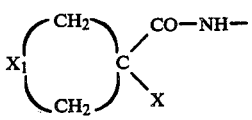
(c)

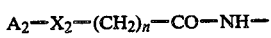
(d)

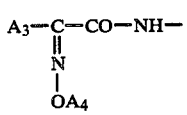
(e)

wherein n is zero, one or two, m is zero, one or two, $A_1$ is alkyl of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or dialkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; and $R^2$ and $R^3$ are independently selected from hydrogen or a hydrocarbon group of 1 to 18 carbon atoms.

8. A composition according to claim 2 wherein $R^1$ is amino, t-butoxycarbonylamino, benzyloxycarbonylamino or benzylideneamino.

9. A composition according to claim 2 wherein $R^1$ is of the sub-formulae (a)-(e):

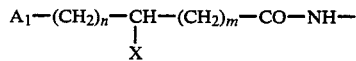  (a)

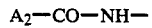  (b)

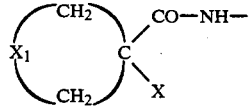  (c)

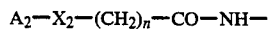  (d)

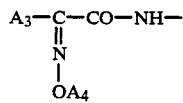  (e)

wherein n is zero, one or two, m is zero, one or two, $A_1$ is alkyl of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or dialkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; and $R^2$ and $R^3$ are independently selected from hydrogen or a hydrocarbon group of 1 to 18 carbon atoms.

10. A method according to claim 4 wherein $R^1$ is amino, t-butoxycarbonylamino, benzyloxycarbonylamino or benzylideneamino.

11. A method according to claim 4 wherein $R^1$ is of the sub-formulae (a)-(e):

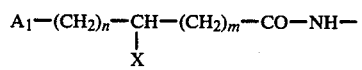  (a)

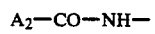  (b)

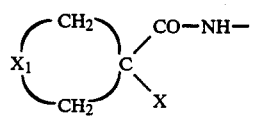  (c)

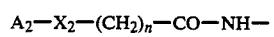  (d)

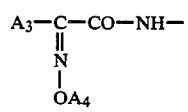  (e)

wherein n is zero, one or two, m is zero, one or two; $A_1$ is alkyl of 1 to 6 carbon atoms, cycloalkyl of 3 to 6 carbon atoms, cycloalkenyl of 4 to 7 carbon atoms, cyclohexadienyl, phenyl, hydroxyphenyl, thienyl or pyridyl; X is a hydrogen, bromo, chloro, carboxy or a pharmaceutically acceptable ester thereof, sulpho, tetrazolyl, azido, hydroxy, acyloxy, amino, acylamino, heterocyclylamino, ureido, guanidino or acylureido group; $A_2$ is phenyl, 2,6-dimethoxy-phenyl, 2-alkoxy-1-naphthyl, 3-arylisoxazolyl, isothiazolyl or 3-aryl-5-methyl isoxazolyl; $X_1$ is $CH_2OCH_2$, $CH_2SCH_2$ or $(CH_2)_n$; $X_2$ is an oxygen or sulphur atom; $A_3$ is phenyl or aminothiazolyl; and $A_4$ is hydrogen, alkyl of 1 to 6 carbon atoms, cycloalkyl of 3 to 6 carbon atoms, arylaminocarbonyl, alkylaminocarbonyl of 1 to 6 carbon atoms, alkanoyl of 1 to 6 carbon atoms, alkoxycarbonyl of 1 to 6 carbon atoms, alkenyl of 2 to 6 carbon atoms, carboxyalkyl of 1 to 6 carbon atoms, alkylsulphonyl of 1 to 6 carbon atoms or di-alkylphosphatomethyl of 1 to 6 carbon atoms in each alkyl moiety; wherein heterocyclyl means a 5- or 6-membered heterocyclyl group containing one to three heteroatoms selected from sulphur, oxygen or nitrogen, said group being optionally substituted by one, two or three substituents selected from hydroxy, amino, halo and alkoxy of 1 to 6 carbon atoms; $R^4$ is a phenyl, thienyl or phenoxy group; $R^5$ is methyl; and $R^2$ and $R^3$ are independently selected from hydrogen or a hydrocarbon group of 1 to 18 carbon atoms.

12. A compound of the formula (II):

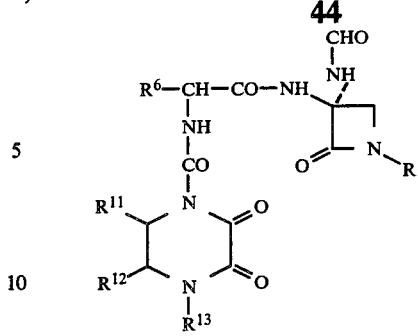

(II)

or a pharmaceutically acceptable salt thereof wherein R is —SO$_3$H; R$^6$ is phenyl, hydroxyphenyl, cyclohexadienyl, or a 5- or 6-membered heterocyclyl group containing one to three heteroatoms selected from sulphur, oxygen or nitrogen, said group being optionally substituted by one, two or three substituents selected from hydroxy, amino, halo and alkoxy; R$^{11}$ and R$^{12}$ are each hydrogen, alkyl of 1 to 6 carbon atoms, halo, amino, hydroxy or alkoxy of 1 to 6 carbon atoms; and R$^{13}$ is hydrogen, alkyl of 1 to 6 carbon atoms or benzyl.

* * * * *

UNITED STATES PATENT AND TRADEMARK OFFICE
CERTIFICATE OF CORRECTION

PATENT NO. : 4,647,558
DATED : March 3, 1987
INVENTOR(S) : PONSFORD ET AL

It is certified that error appears in the above-identified patent and that said Letters Patent are hereby corrected as shown below:

Kindly correct the claims in the above patent to read as follows:

Claim 1, line 2 below the structural formula, "t-butylcar-" should read --t-butoxycar- --.

Claim 2, line 2 below the structural formula, "t-butylcar-" should read --t-butoxycar- --.

Claim 4, line 2 below the structural formula, "t-butylcar-" should read --t-butoxycar- --.

Signed and Sealed this

Twenty-fourth Day of November, 1987

Attest:

DONALD J. QUIGG

Attesting Officer

Commissioner of Patents and Trademarks